(12) United States Patent
Trollsas et al.

(10) Patent No.: US 7,927,621 B2
(45) Date of Patent: Apr. 19, 2011

(54) THIOESTER-ESTER-AMIDE COPOLYMERS

(75) Inventors: Mikael O. Trollsas, San Jose, CA (US);
Nam D. Pham, Dallas, TX (US);
Michael H. Ngo, San Jose, CA (US);
Bozena Zofia Maslanka, Aptos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 499 days.

(21) Appl. No.: 11/821,995

(22) Filed: Jun. 25, 2007

(65) Prior Publication Data

US 2008/0319551 A1    Dec. 25, 2008

(51) Int. Cl.
| | |
|---|---|
| A61K 31/436 | (2006.01) |
| A61K 31/506 | (2006.01) |
| A61K 38/44 | (2006.01) |
| A61K 31/56 | (2006.01) |
| A61K 31/337 | (2006.01) |
| A61F 2/04 | (2006.01) |
| C08G 75/02 | (2006.01) |
| A61P 9/00 | (2006.01) |

(52) U.S. Cl. ...... 424/423; 623/23.7; 424/94.4; 514/180; 514/182; 514/252.18; 514/291; 514/449; 528/290

(58) Field of Classification Search .................... None
See application file for complete search history.

(56) References Cited

U.S. PATENT DOCUMENTS

| | | | |
|---|---|---|---|
| 4,304,767 A | 12/1981 | Heller et al. |
| 4,800,882 A | 1/1989 | Gianturco |
| 4,886,062 A | 12/1989 | Wiktor |
| 5,272,012 A | 12/1993 | Opolski |
| 4,733,665 A | 1/1994 | Palmaz |
| 5,581,387 A | 12/1996 | Cahill |
| 5,702,754 A | 12/1997 | Zhong |
| 5,861,387 A | 1/1999 | Labrie et al. |
| 5,869,127 A | 2/1999 | Zhong |
| 5,997,517 A | 12/1999 | Whitbourne |
| 6,001,117 A | 12/1999 | Huxel et al. |
| 6,099,563 A | 8/2000 | Zhong |
| 6,110,483 A | 8/2000 | Whitbourne et al. |
| 6,179,817 B1 | 1/2001 | Zhong |
| 6,197,051 B1 | 3/2001 | Zhong |
| 6,231,590 B1 | 5/2001 | Slaikeu et al. |
| 6,274,164 B1 | 8/2001 | Novich |
| 6,306,176 B1 | 10/2001 | Whitbourne |
| 6,494,862 B1 | 12/2002 | Ray et al. |
| 6,503,538 B1 | 1/2003 | Chu et al. |
| 6,544,223 B1 | 4/2003 | Kokish |
| 6,544,543 B1 | 4/2003 | Mandrusov et al. |
| 6,656,216 B1 | 12/2003 | Hossainy |
| 6,656,506 B1 | 12/2003 | Wu et al. |
| 6,663,662 B2 | 12/2003 | Pacetti et al. |
| 6,663,880 B1 | 12/2003 | Roorda et al. |
| 6,673,154 B1 | 1/2004 | Pacetti et al. |
| 6,703,040 B2 | 3/2004 | Katsarava |
| 6,712,845 B2 | 3/2004 | Hossainy |
| 6,743,462 B1 | 6/2004 | Pacetti |
| 6,753,071 B1 | 6/2004 | Pacetti |
| 6,758,859 B1 | 7/2004 | Dang et al. |
| 6,790,228 B2 | 9/2004 | Hossainy |
| 6,818,063 B1 | 11/2004 | Kerrigan |
| 6,824,559 B2 | 11/2004 | Michal |
| 6,926,919 B1 | 8/2005 | Hossainy et al. |
| 6,972,054 B2 | 12/2005 | Kerrigan |
| 7,005,137 B1 | 2/2006 | Hossainy et al. |
| 7,022,334 B1 | 4/2006 | Ding |
| 7,056,591 B1 | 6/2006 | Pacetti et al. |
| 7,060,093 B2 | 6/2006 | Dang |
| 7,074,276 B1 | 7/2006 | Van Sciver et al. |
| 7,115,300 B1 | 10/2006 | Hossainy et al. |
| 7,135,038 B1 | 11/2006 | Limon |
| 7,166,680 B2 | 1/2007 | Desnoyer |
| 7,169,178 B1 | 1/2007 | Santos et al. |
| 7,175,874 B1 | 2/2007 | Pacetti |
| 7,201,935 B1 | 4/2007 | Claude et al. |
| 7,217,426 B1 | 5/2007 | Hossainy |
| 7,232,490 B1 | 6/2007 | Hossainy |
| 7,232,573 B1 | 6/2007 | Ding |
| 7,442,384 B2 * | 10/2008 | Loomis et al. ............... 424/423 |
| 2003/0073961 A1 | 4/2003 | Happ |
| 2003/0104028 A1 | 6/2003 | Hossainy et al. |
| 2003/0105518 A1 | 6/2003 | Dutta |
| 2003/0158517 A1 | 8/2003 | Kokish |
| 2003/0190406 A1 | 10/2003 | Hossainy |
| 2004/0047980 A1 | 3/2004 | Pacetti |
| 2004/0052858 A1 | 3/2004 | Wu et al. |
| 2004/0054104 A1 | 3/2004 | Pacetti |

(Continued)

FOREIGN PATENT DOCUMENTS

| | | |
|---|---|---|
| EP | 0 769 512 | 4/1997 |
| WO | WO 2005/000939 | 1/2005 |

OTHER PUBLICATIONS

International Search Report for PCT/US2008/064162, mailed Nov. 3, 2008, 11 pgs.
U.S. Appl. No. 09/406,473, filed Sep. 27, 1999, Pacetti.
U.S. Appl. No. 09/748,412, filed Dec. 21, 2000, Roorda.
U.S. Appl. No. 09/894,293, filed Jun. 27, 2001, Roorda et al.
U.S. Appl. No. 09/966,786, filed Sep. 27, 2001, Hossainy.
U.S. Appl. No. 09/967,632, filed Sep. 28, 2001, Pacetti.
U.S. Appl. No. 10/040,538, filed Dec. 28, 2001, Pacetti et al.
U.S. Appl. No. 10/104,772, filed Mar. 20, 2002, Dutta.
U.S. Appl. No. 10/108,004, filed Mar. 27, 2002, Hossainy et al.
U.S. Appl. No. 10/176,504, filed Jun. 21, 2002, Roorda et al.
U.S. Appl. No. 10/177,154, filed Jun. 21, 2002, Hossainy et al.
U.S. Appl. No. 10/177,942, filed Jun. 21, 2002, Michal et al.
U.S. Appl. No. 10/199,272, filed Jul. 18, 2002, Ding.

(Continued)

*Primary Examiner* — Robert A Wax
*Assistant Examiner* — Danah Al-Awadi
(74) *Attorney, Agent, or Firm* — Squire Sanders & Dempsey (US), LLP

(57) ABSTRACT

A poly(thioester ester amide) copolymer and method of making and using the same are disclosed.

34 Claims, 8 Drawing Sheets

U.S. PATENT DOCUMENTS

| | | |
|---|---|---|
| 2004/0060508 A1 | 4/2004 | Pacetti |
| 2004/0062853 A1 | 4/2004 | Pacetti et al. |
| 2004/0063805 A1 | 4/2004 | Pacetti et al. |
| 2004/0071861 A1 | 4/2004 | Mandrusov |
| 2004/0072922 A1 | 4/2004 | Hossainy |
| 2004/0073298 A1 | 4/2004 | Hossainy |
| 2004/0086542 A1 | 5/2004 | Hossainy |
| 2004/0180132 A1 | 9/2004 | Pacetti |
| 2004/0191405 A1 | 9/2004 | Kerrigan |
| 2004/0253203 A1 | 12/2004 | Hossainy |
| 2005/0021127 A1 | 1/2005 | Kawula |
| 2005/0025799 A1 | 2/2005 | Hossainy |
| 2005/0074544 A1 | 4/2005 | Pacetti et al. |
| 2005/0137381 A1 | 6/2005 | Pacetti |

OTHER PUBLICATIONS

U.S. Appl. No. 10/246,883, filed Sep. 18, 2002, Taylor.
U.S. Appl. No. 10/260,182, filed Sep. 27, 2002, Hossainy.
U.S. Appl. No. 10/266,479, filed Oct. 8, 2002, Hossainy.
U.S. Appl. No. 10/271,851, filed Oct. 15, 2002, Roorda.
U.S. Appl. No. 10/286,058, filed Oct. 31, 2002, Pacetti et al.
U.S. Appl. No. 10/316,739, filed Dec. 10, 2002, Zhang et al.
U.S. Appl. No. 10/327,371, filed Dec. 19, 2002, Lin et al.
U.S. Appl. No. 10/330,412, filed Dec. 27, 2002, Hossainy et al.
U.S. Appl. No. 10/375,496, filed Feb. 26, 2003, Esbeck.
U.S. Appl. No. 10/375,497, filed Feb. 26, 2003, Pacetti.
U.S. Appl. No. 10/376,027, filed Feb. 26, 2003, Kokish et al.
U.S. Appl. No. 10/376,348, filed Feb. 26, 2003, Ding et al.
U.S. Appl. No. 10/382,197, filed Mar. 4, 2003, Pacetti.
U.S. Appl. No. 10/428,691, filed May 1, 2003, Pacetti.
U.S. Appl. No. 10/438,378, filed May 15, 2003, Esbeck et al.
U.S. Appl. No. 10/606,711, filed Jun. 26, 2003, Pacetti.
U.S. Appl. No. 10/606,712, filed Jun. 26, 2003, Pacetti.
U.S. Appl. No. 10/631,116, filed Jul. 31, 2003, Dehnad.
U.S. Appl. No. 10/703,334, filed Nov. 6, 2003, Pacetti.
U.S. Appl. No. 10/705,546, filed Nov. 10, 2003, Kwok et al.
U.S. Appl. No. 10/714,111, filed Nov. 14, 2003, Claude.
U.S. Appl. No. 10/718,278, filed Nov. 19, 2003, Hossainy et al.
U.S. Appl. No. 10/718,976, filed Nov. 20, 2003, Hossainy et al.
U.S. Appl. No. 10/719,516, filed Nov. 21, 2003, Tang et al.
U.S. Appl. No. 10/725,698, filed Dec. 1, 2003, Pacetti.
U.S. Appl. No. 10/729,551, filed Dec. 5, 2003, Pacetti.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/746,483, filed Dec. 24, 2003, Galuser et al.
U.S. Appl. No. 10/750,139, filed Dec. 30, 2003, Desnoyer et al.
U.S. Appl. No. 10/751,043, filed Jan. 2, 2004, Hossainy et al.
U.S. Appl. No. 10/751,289, filed Jan. 2, 2004, Hossainy et al.
U.S. Appl. No. 10/805,036, filed Mar. 16, 2004, Pacetti.
U.S. Appl. No. 10/812,780, filed Mar. 29, 2004, Tang et al.
U.S. Appl. No. 10/813,845, filed Mar. 30, 2004, Pacetti et al.
U.S. Appl. No. 10/815,421, filed Mar. 31, 2004, Hossainy.
U.S. Appl. No. 10/816,072, filed Mar. 31, 2004, Dugan et al.
U.S. Appl. No. 10/820,316, filed Aug. 7, 2004, Hossainy et al.
U.S. Appl. No. 10/835,229, filed Apr. 28, 2004, Prabhu et al.
U.S. Appl. No. 10/835,656, filed Apr. 30, 2004, Tang et al.
U.S. Appl. No. 10/835,912, filed Apr. 30, 2004, Hossainy et al.
U.S. Appl. No. 10/851,411, filed May 20, 2004, Chen.
U.S. Appl. No. 10/853,924, filed May 25, 2004, Pathak.
U.S. Appl. No. 10/855,294, filed May 26, 2004, Pacetti et al.
U.S. Appl. No. 10/877,419, filed Jun. 25, 2004, Pacetti.
U.S. Appl. No. 10/881,540, filed Jun. 29, 2004, Hossainy et al.
U.S. Appl. No. 10/882,506, filed Jun. 30, 2004, Stewart et al.
U.S. Appl. No. 10/883,242, filed Jun. 30, 2004, Roorda et al.
U.S. Appl. No. 10/902,982, filed Jul. 30, 2004, Pacetti et al.
U.S. Appl. No. 10/909,795, filed Jul. 30, 2004, Ding et al.
U.S. Appl. No. 10/910,453, filed Aug. 2, 2004, Hossainy et al.
U.S. Appl. No. 10/913,607, filed Aug. 5, 2004, Pacetti et al.
U.S. Appl. No. 10/928,587, filed Aug. 26, 2004, Hossainy et al.
U.S. Appl. No. 10/931,927, filed Aug. 31, 2004, Pacetti.
U.S. Appl. No. 10/932,364, filed Aug. 31, 2004, Foreman et al.
U.S. Appl. No. 10/948,036, filed Sep. 22, 2004, Pacetti et al.
U.S. Appl. No. 10/975,247, filed Oct. 27, 2004, Desnoyer et al.
U.S. Appl. No. 10/976,550, filed Oct. 29, 2004, Pacetti et al.
U.S. Appl. No. 10/976,551, filed Oct. 29, 2004, DesNoyer et al.
U.S. Appl. No. 10/999,391, filed Nov. 29, 2004, Hossainy.
U.S. Appl. No. 10/978,031, filed Oct. 29, 2004, Pacetti.
U.S. Appl. No. 11/000,572, filed Nov. 30, 2004, Pacetti.
U.S. Appl. No. 11/015,313, filed Dec. 16, 2004, Pacetti et al.
U.S. Appl. No. 11/021,775, filed Dec. 22, 2004, Pacetti.
U.S. Appl. No. 11/023,837, filed Dec. 27, 2004, Hossainy.
U.S. Appl. No. 11/027,822, filed Dec. 29, 2004, Ding.
U.S. Appl. No. 11/027,955, filed Dec. 30, 2004, Hossainy et al.
U.S. Appl. No. 11/035,816, filed Jan. 14, 2005, Hossainy.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Moreno et al., *Macrophage Infiltration Predicts Restenosis After Coronary Intervention in Patients with Unstable Angina*, Circulation, vol. 94, No. 12, (1996) pp. 3098-3102.
Oikawa et al., Mechanisms of Acute Gain and Late Lumen Loss After Atherectomy in Different Preintervention Arterial Remodeling Patterns, *The Am. J. of Cardilogy*, vol. 89, (2002) pp. 505-510.
Scully et al., *Effect of a heparan sulphate with high affinity for antithrombin III upon inactivation of thrombin and coagulaton Factor Xa*, Biochem J. 262, (1989) pp. 651-658.
Virmani et al., *Lessons From Sudden Coronary Death a Comprehensive Morphological Classification Scheme for Atherosclerotic Lesions*, Arterioscler Thromb Vasc Biol. (2000) pp. 1262-1275.

* cited by examiner

THIOESTER-ESTER-AMIDE COPOLYMERS

FIELD OF THE INVENTION

This invention generally relates to thioester-ester-amide copolymers, which is a biomaterial that can be used in biomedical applications such as coating a stent.

DESCRIPTION OF THE BACKGROUND

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Although stents work well mechanically, the chronic issues of restenosis and, to a lesser extent, stent thrombosis remain. Pharmacological therapy in the form of a drug delivery stent appears to be a feasible means to tackle these issues. Polymeric coatings placed onto the stent serve to act both as the drug reservoir and to control the release of the drug. One of the commercially available polymer-coated products is a stent manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

The nature of the coating polymers plays an important role in defining the surface properties of a coating. For example, coating integrity depends largely on the nature of the polymer forming the coating. For example, a very low $T_g$, amorphous coating material can have unacceptable rheological behavior upon mechanical perturbation such as crimping, balloon expansion, etc. On the other hand, a high $T_g$ or highly crystalline coating material introduces brittle fractures in the high strain areas of the stent pattern.

Therefore, there is a need for polymeric materials that can be tailored to meet need of a coating on a medical device.

The polymer and methods of making the polymer disclosed herein address the above-described problems.

SUMMARY OF THE INVENTION

Provided herein is a poly(thioester ester amide) comprising units derived from an aliphatic dithiol and units derived from ester containing di-amine functional as well as activated carboxylic di-acids monomer(s).

The poly(thioester ester amide) can form compositions that are biomaterials that can be used for forming fiber, film, coating, particle, and/or gel in many biomedical applications. In addition, a polymer comprising thioester units can have short hydrolysis half-life time, thus allowing the polymer to have tunable degradation rate. The polymer can be used for drug delivery, allowing control of drug release by controlled erosion of the polymer.

In some embodiments, the polymer described herein can be used to form a coating on an implantable device, which can optionally include a bioactive agent. The bioactive agent can be any diagnostic agent, therapeutic agent, or preventive agent. Some examples of such bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, dexamethasone acetate, other dexamethasone derivatives, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), TAFA-93, biolimus-7, biolimus-9, clobetasol, momethasone derivatives, pimecrolimus, imatinib mesylate, midostaurin, prodrugs thereof, co-drugs thereof, or combinations thereof. In some embodiments, the hydrophilic bioactive agent can be a peptide (e.g., RGD, cRGD or mimetics thereof), a protein (e.g., IGF, HGF, VEGF) or a drug carrying a charge.

A medical device having a coating that includes a thioester containing polymer described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

DETAILED DESCRIPTION

Figure 1A:
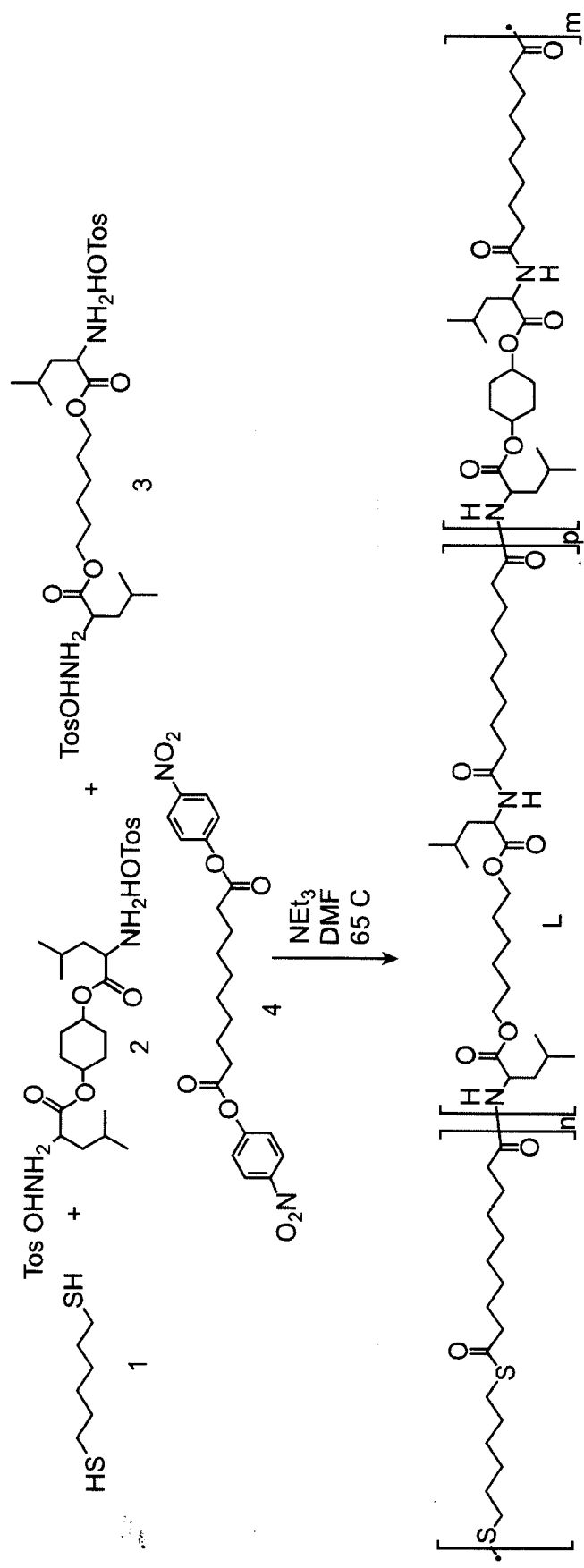
FIG. 1A shows a reaction scheme for synthesizing a PTEA polymer.

Provided herein is a poly(thioester ester amide) comprising units derived from an aliphatic dithiol and units derived from ester containing di-amine functional as well as activated carboxylic di-acids monomer(s).

The poly(thioester ester amide) (PTEA) can form compositions that are biomaterials that can be used for forming fiber, film, coating, particle, and/or gel in many biomedical applications. In addition, a polymer comprising thioester units can have short hydrolysis half-life time, and the PTEA can have different molecular weight and glass transition temperature ($T_g$), depending on reaction conditions and concentration of monomers, respectively. Therefore, the PTEA polymer described herein can have tunable mechanical properties, tunable degradation rate, and/or tunable release rate of a drug or agent included in a coating or matrix including the PTEA polymer. Thus, for example, the polymer can be used for drug delivery, allowing control of drug release by controlled erosion of the polymer.

In some embodiments, the polymer described herein can be used to form a coating on an implantable device, which can optionally include a bioactive agent. The bioactive agent can be any diagnostic agent, therapeutic agent, or preventive agent. Some examples of such bioactive agents include, but are not limited to, paclitaxel, docetaxel, estradiol, nitric oxide donors, super oxide dismutases, super oxide dismutases mimics, 4 amino-2,2,6,6-tetramethylpiperidine-1-oxyl (4-amino-TEMPO), tacrolimus, dexamethasone, dexamethasone acetate, other dexamethasone derivatives, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), TAFA-93, biolimus-7, biolimus-9, clobetasol, momethasone derivatives, pimecrolimus, imatinib mesylate, midostaurin, prodrugs thereof, co-drugs thereof, or combinations thereof. In some embodiments, the hydrophilic bioactive agent can be a peptide (e.g., RGD, cRGD or mimetics thereof), a protein (e.g., IGF, HGF, VEGF), or a drug carrying a charge.

A medical device having a coating that includes a polymer with thioester units described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

Poly(Thioester Ester Amide) (PTEA) Polymers

The PTEA material described herein generally includes at least one thioester moiety or repeating unit, at least one ester moiety or repeating unit and at least one amide moiety or repeating unit. An example of the polymer comprises a structure of Formula I:

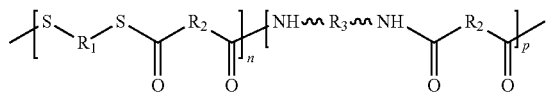

Formula I

In formula I:

$R_1$ originates from an aliphatic dithiol. The aliphatic dithiol can be straight chained or branched. In some embodiments, the aliphatic dithiol can be a cyclic aliphatic dithiol, including a cyclic alkyl group(s). In some embodiments, the aliphatic dithiol can include electronic unsaturation including, e.g., C=C bond(s). In some embodiments, the aliphatic dithiol can include arylalkyl groups. In some embodiments, $R_1$ has a general formula of Formula II —$(CH_2)_m$— where m is a positive integer ranging from 1 to 100, e.g., 2, 3, 4, 5, 6, 7, 8, 9, 10, 11, 12, 13, 14, 15, 16, 17, 18, 19, or 20. In some embodiments, $R_1$ can include a heteroatom(s) such as oxygen, halo atom(s) (F, Cl, Br or I), S, and N. In some embodiments $R_1$ can be generated from a mixture of two or more of the dithiols discussed above. In some embodiments, $R_1$ can specifically exclude any of the groups described herein;

$R_2$ can originate from any organic diacid. For example, $R_2$ can be the aliphatic part of a diacid. The aliphatic diacid can be straight chained or branched. In some embodiments, the aliphatic diacid can be a cyclic aliphatic diacid, including a cyclic alkyl group(s). In some embodiments, the aliphatic diacid can include electronic unsaturation including, e.g., C=C bond(s). In some embodiments, the aliphatic diacid can include arylalkyl groups. In some embodiments, $R_2$ has a general formula of Formula II —$(CH_2)_m$— where m is a positive integer ranging from 1 to 100, e.g., 2, 3, 4, 5, 6, 7, 8, 9, 10, 11, 12, 13, 14, 15, 16, 17, 18, 19, or 20. In some embodiments, $R_2$ can include a heteroatom(s) such as oxygen, halo atom(s) (F, Cl, Br or I), S, and N. In some embodiments, $R_2$ can include aromatic groups such as phenyl or naphthyl groups. The aromatic groups can further include substituents such as alkyl, halo atom(s) (F, Cl, Br or I), carboxyl, hydroxyl, phosphoryl, sulfonyl, carbonyl, amino, amide, ether, nitro, azo, or combinations thereof. In some embodiments $R_2$ can be generated from a mixture of two or more of the organic diacids discussed above. In some embodiments, $R_2$ can specifically exclude any of the groups described herein;

n and p are independent positive integers ranging from 1 to about 10,000, e.g., from about 10 to about 10,000, from about 20 to about 10,000, from about 50 to about 10,000, from about 100 to about 10,000, from about 500 to about 10,000, or from about 1000 to about 10,000. In some embodiments, n and p can be an integer from about 10 to about 1000, from about 20 to about 1000, from about 50 to about 1000, or from about 100 to about 1000. Some exemplary values for n and/or p are about 10, about 30, about 50, about 60, about 70, about 80, about 90, about 200, about 300, about 400, about 600, about 700, about 800, about 900, about 1500, about 2000, about 3000, about 4000, about 5000, about 6000, about 7000, about 8000, or about 9000; and $R_3$ is a moiety or repeating unit that includes two terminal groups selected from amine, hydroxyl groups, or combinations thereof;

In some embodiments, the PTEA polymer can be generated from two or more different diol/diamine units or blocks. An example of the polymer of Formula I is shown below:

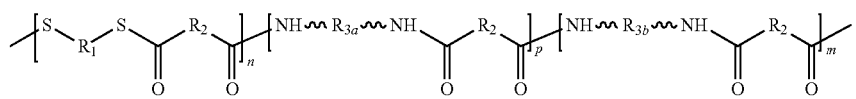

Formula III where:

n and p are as defined above;

m is an integer ranging from 0 to about 10,000, e.g., from about 10 to about 10,000, from about 20 to about 10,000, from about 50 to about 10,000, from about 100 to about 10,000, from about 500 to about 10,000, or from about 1000 to about 10,000. In some embodiments, m can be an integer from about 1 to about 1000, from about 20 to about 1000, from about 50 to about 1000, or from about 100 to about 1000. Some exemplary values for m are about 10, about 30, about 50, about 60, about 70, about 80, about 90, about 200, about 300, about 400, about 600, about 700, about 800, about 900, about 1500, about 2000, about 3000, about 4000, about 5000, about 6000, about 7000, about 8000, or about 9000; and $R_{3a}$ and $R_{3b}$ are independently moieties or repeating units that include two terminal groups selected from amine, hydroxyl groups, or combinations thereof.

In some embodiments, R, including $R_3a$ and $R_{3b}$, can specifically exclude any of the groups described herein;

In some embodiments, the PTEA polymer can include three or more different $R_3$ units or blocks. As used herein, $R_3$ refers to a compound having the general structure of formula IV:

Formula IV

In some embodiments, $R_3$ can be a condensation product of two molar equivalents of an amino acid with one molar equivalent of a diol. In some embodiments, $R_3$ can be a condensation product of one molar equivalent of a first amino acid, one molar equivalent of a second amino acid, and one molar equivalent of a diol.

In some embodiments, $R_3$ can be a condensation product of two molar equivalents of an amino acid with one molar equivalent of a mixture of a first diol and a second diol. In some embodiments, $R_3$ can be a condensation product of one molar equivalent of an amino acid and one molar equivalent of a mixture of a first diol and a second diol.

In some embodiments, the PTEA polymer described herein can have been generated from two or more dithiol units or moieties. In some embodiments, the PTEA polymer can include two, three, or more ester-amine units or moieties.

In some embodiments, the PTEA polymer described herein can have been generated from two or more diacid units or moieties. In some embodiments, the PTEA polymer can include two, three, or more diacid units or moieties.

The PTEA polymer can be a random, block or alternating copolymer of the thioester unit(s) or moiety(ies) and the ester containing amide unit(s) or moiety(ies).

Some examples of the ester amide units, include, but are not limited to, the ones shown below (Table 1), which are formed of racemic or enantiomeric pure amino acids, diols and activated diacids.

TABLE 1

Exemplary ester amide units

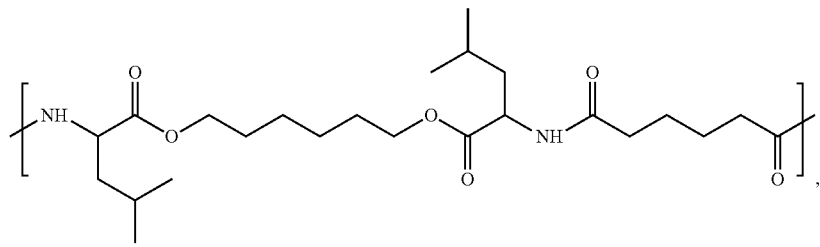

[EA I]

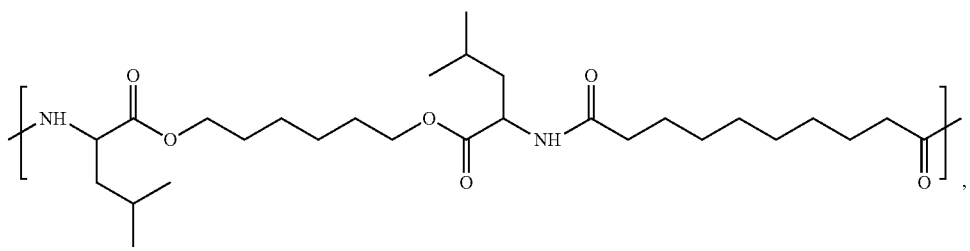

[EA II]

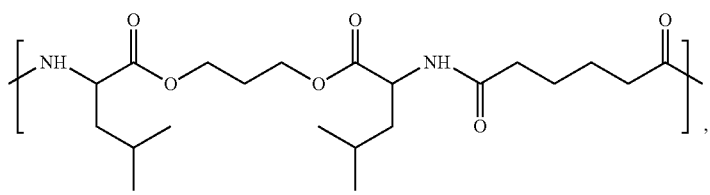

[EA III]

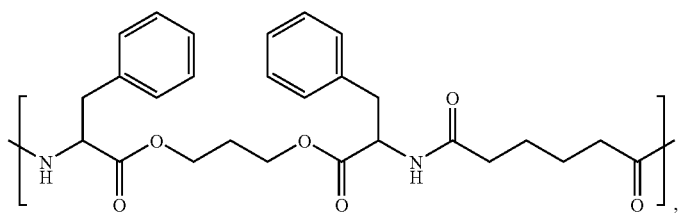

[EA IV]

TABLE 1-continued
Exemplary ester amide units
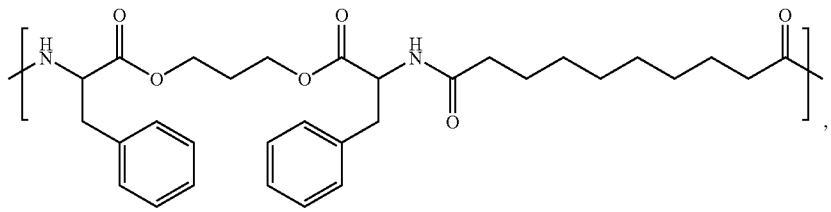
[EA V]
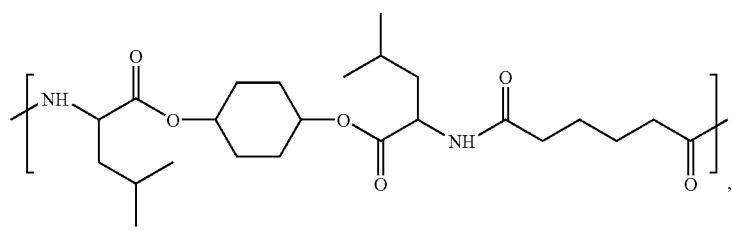
[EA VI]
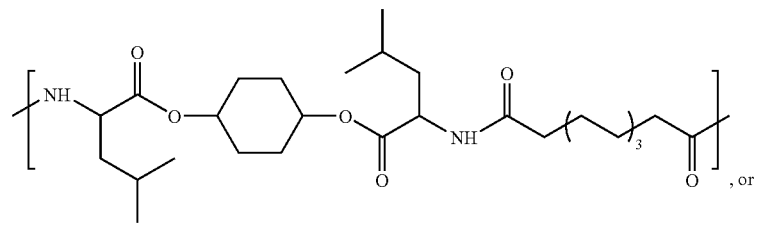
[EA VII]
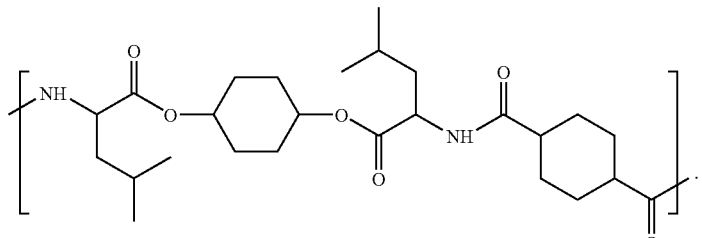
[EA VIII]
Some exemplary thioester units are shown below (Table 2).
TABLE 2
Exemplary thioester units
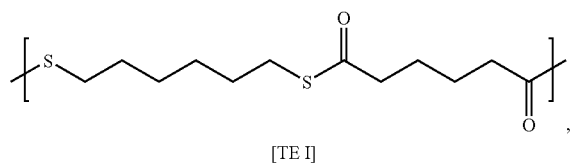
[TE I]
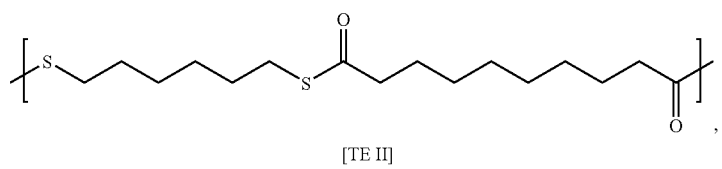
[TE II]

TABLE 2-continued

Exemplary thioester units

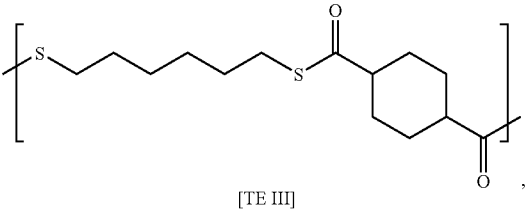

[TE III]

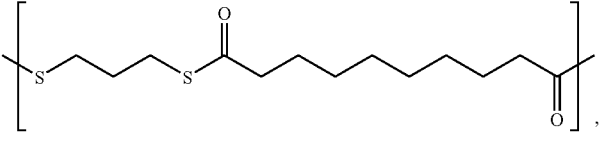

[TE IV]

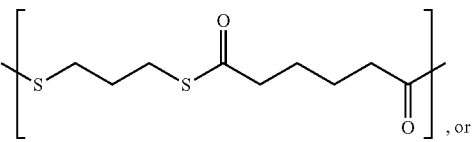

[TE V]

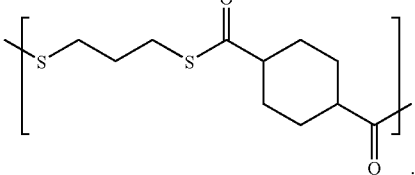

[TE VI]

Examples of the PTEA polymer described herein include, but are not limited to, a PTEA copolymer that includes at least one EA units selected from [EA I], [EA II], [EA III], [EA IV], [EA V], [EA VI], [EA VII], shown in Table 1, or combinations thereof and at least one TE unit selected from [TE I], [TE II], [TE III], [TE IV], [TE V], [TE VI], shown in Table 2, or combinations thereof. In some embodiments, the PTEA copolymer can have a formula as shown in Table 3.

TABLE 3

Some examples of PTEA polymers

-[TE I]$_n$-[EA I]$_p$-[EA IV]$_m$-,
-[TE I]$_n$-[EA III]$_p$-[EA IV]$_m$-,
-[TE I]$_n$-[EA I]$_p$-[EA VI]$_m$-,
-[TE I]$_n$-[EA II]$_p$-,
-[TE I]$_n$-[EA III]$_p$-,
-[TE I]$_n$-[EA IV]$_p$-,
-[TE I]$_n$-[EA VI]$_p$-,
-[TE III]$_n$-[EA II]$_p$[EA IV]$_m$-,
-[TE III]$_n$-[EA II]$_p$-[EA VII]$_m$-,
-[TE III]$_n$-[EA II]$_p$-,
-[TE III]$_n$-[EA VII]$_p$-,
-[TE III]$_n$-[EA V]$_p$-,
-[TE III]$_n$-[EA V]$_p$-,
-[TE III]$_n$-[TE I]$_h$-[EA IV]$_p$-[EA V]$_m$-, or
-[TE III]$_n$-[TE I]$_h$-[EA VI]$_p$-[EA VII]$_m$-[EA II]$_k$-[EA I]$_o$-,
-[TE I]$_n$-[TE V]$_o$-[EA I]$_p$-[EA IV]$_m$-,
-[TE I]$_n$-[TE V]$_o$-[EA III]$_p$-[EA IV]$_m$-,
-[TE I]$_n$-[TE V]$_o$-[EA I]$_p$-[EA VI]$_m$-,
-[TE I]$_n$-[TE V]$_o$-[EA I]$_p$-,

TABLE 3-continued

Some examples of PTEA polymers

-[TE I]$_n$-[TE V]$_o$-[EA III]$_p$-,
-[TE I]$_n$-[TE V]$_o$-[EA IV]$_p$-,
-[TE I]$_n$-[TE V]$_o$-[EA VI]$_p$-,
-[TE III]$_n$-[TE IV]$_o$-[EA II]$_p$[EA IV]$_m$-,
-[TE III]$_n$-[TE IV]$_o$-[EA II]$_p$-[EA VII]$_m$-,
-[TE III]$_n$-[TE IV]$_o$-[EA II]$_p$-,
-[TE III]$_n$-[TE IV]$_o$-[EA VII]$_p$-,
-[TE III]$_n$-[TE IV]$_o$-[EA V]$_p$-,
-[TE III]$_n$-[TE IV]$_o$-[EA V]$_p$-,
-[TE III]$_n$-[TE I]$_h$-[TE IV]$_g$-[TE V]$_o$-[EA IV]$_p$-[EA V]$_m$-, or
-[TE III]$_n$-[TE I]$_h$-[TE IV]$_g$-[TE V]$_o$-[EA VI]$_p$-[EA VII]$_m$-[EA II]$_k$-[EA I]$_f$-,

In Table 3, n, p, m, h, g, f, k, and o are independent integers defined below:

The values of n, g, o, and h can range from 0 to about 10,000, e.g., from 1 to about 10,000, from about 10 to about 10,000, from about 20 to about 10,000, from about 50 to about 10,000, from about 100 to about 10,000, from about 500 to about 10,000, or from about 1000 to about 10,000. In some embodiments, n, g, o, and h can be an integer from about 10 to about 1000, from about 20 to about 1000, from about 50 to about 1000, or from about 100 to about 1000. Some exemplary values for n and/or h are about 10, about 30, about 50, about 60, about 70, about 80, about 90, about 200, about 300, about 400, about 600, about 700, about 800, about 900, about 1500, about 2000, about 3000, about 4000, about 5000, about 6000, about 7000, about 8000, or about 9000;

p, m, f and k are independent integers ranging from 0 to about 10,000, e.g., from about 10 to about 10,000, from about 20 to about 10,000, from about 50 to about 10,000, from about 100 to about 10,000, from about 500 to about 10,000, or from about 1000 to about 10,000. In some embodiments, p, m, f and k can be integers from about 1 to about 1000, from about 20 to about 1000, from about 50 to about 1000, or from about 100 to about 1000. Some exemplary values for p, m, f and k are about 10, about 30, about 50, about 60, about 70, about 80, about 90, about 200, about 300, about 400, about 600, about 700, about 800, about 900, about 1500, about 2000, about 3000, about 4000, about 5000, about 6000, about 7000, about 8000, or about 9000;

The sum of $n+g+o+h \geq 1$ or above; and

The sum of $p+m+f+k \geq 1$ or above.

Some other examples units that can be included in a PTEA polymer described herein can be derived from reagents described below in Tables 4-8. For convenience, these reagents are sometimes referred to as A, B, C, or D reagents, as defined below. For example, Table 4 provides some exemplary diamine reagents that can be included in the PTEA polymer described herein.

TABLE 4

| No. | Code | Reagent General Formula |
|---|---|---|
| 1 | $A_1$ | 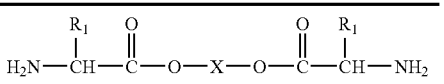 |
| 2 | $A_2$ | $H_2N-Y-NH_2$ |

In the general formulae of compounds $A_1$, and $A_2$ in Table 4, the substitutents $R_1$, $R_2$, X, and Y can be as follows:

$R_1$—(a) hydrogen;
(b) methyl (—$CH_3$);
(c) iso-propyl (-i-$C_3H_7$);
(d) sec-butyl (-sec-$C_4H_9$);
(e) iso-butyl (-i-$C_4H_9$); or
(f) benzyl (—$CH_2C_6H_5$);

X—straight chained, cyclic, or branched aliphatic alkylene group $C_nH_{2n}$, wherein n is an integer between 2 and 16, e.g., methylene, ethylene, propylene, butylene, amylene (pentylene), hexylene, cyclo-hexylene, heptylene, octylene, cyclo-hexanedimethylene-, nonylene, decylene, undecylene, or dodecylene group, alternatively the X unit can be a diol with pendant functional groups such as carboxylic acids, an example would include bis-methylol propionic acid (bis-MPA); and Y—straight chained, cyclic, or branched aliphatic alkylene group $C_2H_4$ (ethylene), $C_3H_6$ (propylene), $C_4H_8$ (butylene), $C_5H_{10}$ (pentylene also known as amylene), $C_6H_{10}$ (cyclohexylene), or $C_8H_{14}$ (dimethylene cyclo-hexane).

In some embodiments, the reagent $A_1$ can be synthesized by condensation of two molar equivalents of an amino acid and one molar equivalent of a diol. The synthesis can be carried under the conditions favoring esterification of the amino acid via the amino acid's carboxyl group. The reaction can be conducted under dehydrating conditions which include anhydrous environment and an elevated temperature, for example, about 130° C., and can be catalyzed by a strong acid or base, e.g., p-toluenesulfonic acid.

The diol that can be used to make the reagent $A_1$ has the formula HO—X—OH, where X is as defined above. Representative examples of diols that can be used include ethylene glycol, 1,3-propanediol, 1,4-butane diol, 1,5-pentanediol, 1,6-hexanediol, 1,4-cyclohexanediol, 1,3-cyclohexanediol, 1,7-heptanediol, 1,8-octanediol, 1,9-nonanediol, 1,10-decanediol, 1,11-undecanediol, 1,12-dodecanediol, and bis-methylol propionic acid (bis-MPA). Some exemplary amino acids that can be used to make the reagent $A_1$ have the general formula $H_2N$—$CHR_1$—COOH, where $R_1$ is as defined above. Some amino acids that can be used are provided in Table 5.

TABLE 5

| | | Amino Acid ($H_2N$—CH($R_1$)—COOH) | |
|---|---|---|---|
| No. | $R_1$ | Formula | Name |
| 1 | —H | $H_2N$—$CH_2$—COOH | glycine |
| 2 | —$CH_3$ | 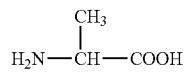 | alanine |
| 3 | -i-$C_3H_7$ | 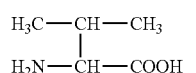 | valine |
| 4 | —sec-$C_4H_9$ | 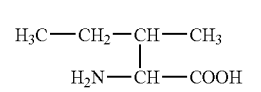 | isoleucine |
| 5 | —i-$C_4H_9$ | 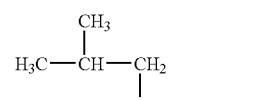 | leucine |
| 6 | $C_6H_5CH_2$— | 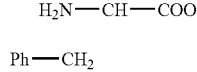 | phenyl alanine |
| 7 | —$(CH_2)_2$—S—$CH_3$ | 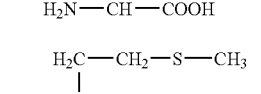 | methionine (α-amino-γ-methylmercaptobutyric acid) |

TABLE 5-continued

| | | Amino Acid ($H_2N-CH(R_1)-COOH$) | |
|---|---|---|---|
| No. | $R_1$ | Formula | Name |
| 8 | $-CH_2-C(O)-NH_2$ | $H_2C-C(O)-NH_2$<br>$\|$<br>$H_2N-CH-COOH$ | asparagine (α-amino-succinamic acid) |
| 9 | $-(CH_2)_2-C(O)-NH_2$ | $H_2C-CH_2-C(O)-NH_2$<br>$\|$<br>$H_2N-CH-COOH$ | glutamine (2-amino-glutaramic acid) |

In addition to amino acids listed in Table 5, other amino acids can be used. One example of such alternative amino acids is proline (2-pyrrolidine carboxylic acid). Other alternative amino acids that can be used include some amino acids having free hydroxyl groups or second carboxyl groups if the free hydroxyl groups or the second carboxyl groups are protected first. Sometimes, the protection is needed so as to avoid interference when reagent $A_1$ is subsequently reacted with other reagents. Examples of the amino acids that can be used after the free hydroxyl or second carboxyl groups are protected include tyrosine, serine, or glutamic acid. In some embodiments, the PTEA polymer can include units derived from a diamine shown in Table 6, which is also sometimes referred to as "group B reagent(s)".

TABLE 6

| No. | Code | Reagent General Formula | Exemplary Reagent Definition ($R_4$ = PEG) |
|---|---|---|---|
| 1 | $B_1$ | $H_2N-\overset{R_1}{\underset{\|}{CH}}-\overset{O}{\underset{\|}{C}}-O-R_2-O-\overset{O}{\underset{\|}{C}}-\overset{R_1}{\underset{\|}{CH}}-NH_2$ | PEG-diester-diamine |
| 2 | $B_2$ | $H_2N-R_2-NH_2$ | PEG-diamine |

In general formulae of compounds $B_1$ and $B_2$ in Table 6, $R_1$ is as defined above. $R_2$ can be a polymer chain. One example of the $R_2$ is a moiety derived from poly(ethylene glycol) (PEG). Alternatively, other biologically beneficial moieties can be used as $R_2$, for example, moieties derived from poly(propylene glycol) (PPG), random or block copolymers of PEG and PPG.

The reagent $B_1$ can be a PEG-diester-diamine adduct (i.e., when $R_4$=PEG) that can be synthesized by condensation of two molar equivalents of an amino acid and one molar equivalent of PEG or alternatively synthesized by condensation of two molar equivalents of an amino acid and one molar equivalent of a mono-disperse oligoethyleneglycol. The synthesis can be carried under the conditions favoring esterification of the amino acid via the carboxyl group. The reaction can be conducted under dehydrating conditions which include anhydrous environment and an elevated temperature, for example, about 130° C., and can be catalyzed by a strong acid or base, e.g., p-toluenesulfonic acid. To make the reagent $B_1$, PEG or the oligoethyleneglycol having molecular weight between about 100 and 4,000 Daltons, for example, about 300 Daltons, can be used. Any amino acid listed in Table 5 can be used. Alternatively, other amino acids can be used, for example, tyrosine, serine, or glutamic acid, if free hydroxyl groups of tyrosine and serine or the second carboxyl group of glutamic acid are protected so as not to interfere when reagent $B_1$ is subsequently reacted with reagents of groups A and C, as discussed above.

PEG terminated with amino groups on both ends (PEG-diamine reagent $B_2$) can be obtained from Huntsman Chemical Co. of Houston, Tex. under the trade name JEFFAMINE.

In some embodiments, the PTEA polymer described herein can include units derived from dicarboxylic acids shown in Table 7, which is sometimes also referred to as "the group C reagent(s)".

TABLE 7

| No. | Code | Reagent General Formula | Reagent Definition |
|---|---|---|---|
| 1 | $C_1$ | $HO-\overset{O}{\underset{\|}{C}}-R_1-\overset{O}{\underset{\|}{C}}-OH$ | Dicarboxylic acid |
| 2 | $C_2$ | $HO-\overset{O}{\underset{\|}{C}}-PEG-\overset{O}{\underset{\|}{C}}-OH$ | PEG-dicarboxylic acid |

In general formula of compound C, presented in Table 7, $R_1$ can be a covalent bond, or a straight chained or branched aliphatic alkylene group $C_nH_m$, wherein n is an integer having a value between 0 and 12, e.g. a single bond (n=0), methylene, ethylene, propylene, butylene, amylene (pentylene), hexylene, heptylene, octylene, nonylene, decylene, undecylene, or dodecylene group, or an aromatic group, e.g., phenyl orparaphenylene. Some examples of dicarboxylic acids are summarized in Table 8.

TABLE 9

| | | Dicarboxylic Acid (HOOC—$R_3$—COOH) | |
|---|---|---|---|
| No. | $R_3$ | Formula | Name |
| 1 | $-(CH_2)_2-$ | $HOOC-(CH_2)_2-COOH$ | succinic (butanedioic) acid |
| 2 | $-CH_2CCH_3ORCH_2-$ | $HOOC-CH_2CCH_3ORCH_2-COOH$ | |
| 3 | $-(CH_2)_4-$ | $HOOC-(CH_2)_4-COOH$ | adipic (hexanedioic) acid |

TABLE 9-continued

| | | Dicarboxylic Acid (HOOC—$R_3$—COOH) | |
|---|---|---|---|
| No. | $R_3$ | Formula | Name |
| 4 | —$(CH_2)_8$— | HOOC—$(CH_2)_8$—COOH | sebacic (decanedioic) acid |
| 5 | (p)-$C_6H_4$— | HOOC-(p)$C_6H_4$—COOH | terephthalic (1,4-benzene dicarboxylic) acid |
| 6 | —$CH(CH_2)_4CH$— | HOOC—$CH(CH_2)_4CH$—COOH | cyclohexane dicarboxylic acid |

Some other examples of dicarboxylic acids that can be also used include oxalic acid, malonic acid, glutaric acid, pimelic acid, suberic acid, or azelaic acid.

The reagents for forming units in the PTEA polymer described herein, including the groups A, B, and C reagents, described above, and dithiols (D) may themselves contain hydrolysable bonds, i.e. ester, anhydride, thioester or amide bonds. Some examples of PTEA can include units derived from combinations of reagents shown below.

(A) Some exemplary PTEA polymers can include units having amide and thioester bonds derived from combination of reagents:
(1) $A_1$, $C_1$ and D ($A_1$-$C_1$-D);
(2) $A_1$, $B_1$ $C_1$ and D ($A_1$-$B_1$-$C_1$-D);
(3) $A_2$, $C_1$ and D ($A_2$-$C_1$-D);
(4) $A_2$, $B_1$ $C_1$ and D ($A_2$-$B_1$-$C_1$-D);
(5) $A_1$, $B_2$ $C_1$ and D ($A_1$-$B_1$-$C_1$-D);
(6) $A_2$, $B_2$ $C_1$ and D ($A_2$-$B_1$-$C_1$-D);
(7) $A_1$, $A_2$, $C_2$ and D ($A_1$-$A_2$-$C_2$-D);
(8) $A_1$, $A_2$, $B_1$ $C_1$ and D ($A_1$-$A_2$-$B_1$-$C_1$-D);
(9) $A_1$, $A_2$, $C_1$ and D ($A_1$-$A_2$-$C_1$-D);
(10) $A_1$, $A_2$, $B_2$, $C_1$ and D ($A_1$-$A_2$-$B_1$-$C_1$-D);
(11) $A_2$, $B_2$ $C_1$ and D ($A_1$-$A_2$-$B_1$-$C_1$-D);

(B) Some exemplary PTEA polymers can include units having amide and thioester bonds derived from combination of reagents:
(1) $A_2$, $B_2$ $C_1$ and D ($A_2$-$B_2$-$C_1$-D); and
(2) $A_2$, $C_2$ and D ($A_2$-$C_2$-D).
(3) $A_1$, $A_2$, $B_2$, $C_1$ and D ($A_1$-$A_2$-$B_2$-$C_1$-D); and
(4) $A_1$, $A_2$, $C_2$ and D ($A_1$-$A_2$-$C_2$-D).

(C) Some exemplary PTEA polymers can include units having amide and thioester bonds derived from combination of reagents:
(1) $A_1$, $C_1$ and D ($A_1$-$C_1$-D);
(2) $A_1$, $B_1$, $C_1$ and D ($A_1$-$B_1$-$C_1$-D);
(3) $A_1$, $B_2$, $C_1$ and D ($A_1$-$B_2$-$C_1$-D);
(4) $A_2$, $C_1$ and D ($A_2$-$C_1$-D);
(5) $A_2$, $B_1$, $C_1$ and D ($A_2$-$B_1$-$C_1$-D);
(6) $A_2$, $B_2$, $C_1$ and D ($A_2$-$B_2$-$C_1$-D);
(7) $A_2$, $C_1$ and D ($A_1$-$C_1$-D);
(8) $A_1$, $A_2$, $C_1$ and D ($A_1$-$A_2$-$C_1$-D);
(9) $A_1$, $A_2$, $B_1$, $C_1$ and D ($A_1$-$A_2$-$B_1$-$C_1$-D);
(10) $A_1$, $A_2$, $B_2$, $C_1$ and D ($A_1$-$A_2$-$B_2$-$C_1$-D);
(11) $A_1$, $B_1$ $B_2$, $C_1$ and D ($A_1$-$B_1$-$B_2$-$C_1$-D);
(12) $A_2$, $B_1$, $B_2$, $C_1$ and D ($A_2$-$B_1$-$B_2$-$C_1$-D);
(13) $A_1$, $A_2$, $B_1$, $B_2$, $C_1$ and D ($A_1$-$A_2$-$B_1$-$B_2$-$C_1$-D).

Preparation of PTEA Polymers

The PTEA polymers described herein can be synthesized according to any established method of forming a condensation type of polymer (see, e.g., *Polymer Chemistry, An Introduction*, M. P. Stevens, Oxford University Press, New York, 1999). For example, for forming a block PTEA copolymer, blocks including the various units defined above can be sequentially incorporated into a the PTEA polymer. For forming a random PTEA copolymer, monomers forming the various units defined above can be simultaneously or sequentially polymerized to form the PTEA block polymer.

Following the polymerization shown in Scheme I, the various polymers shown in Table 3 can be readily synthesized.

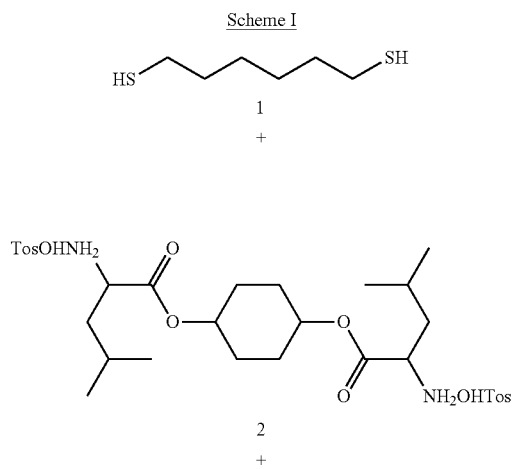

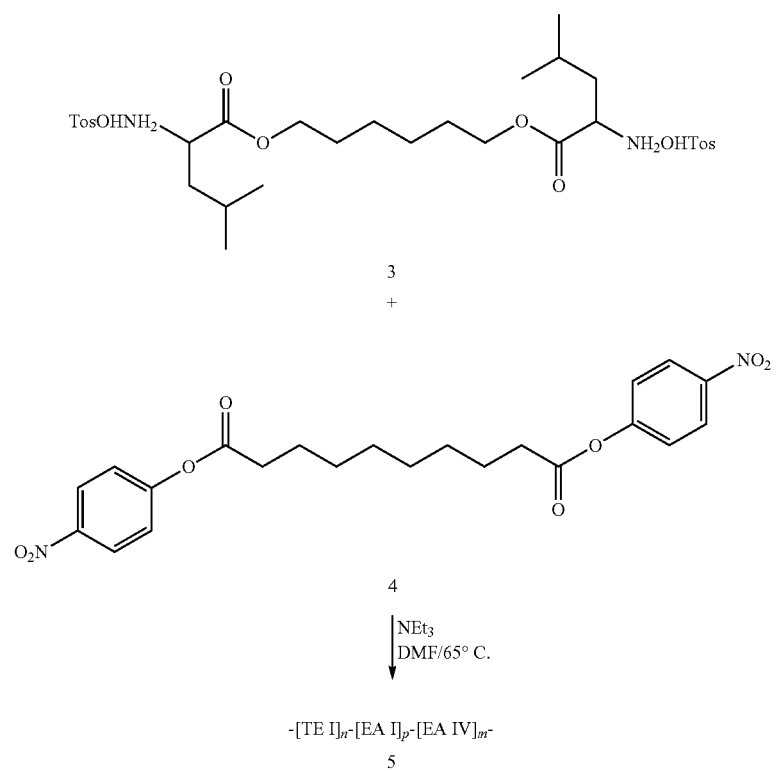
In some embodiments, the method shown in Scheme I can be modified to form polymers with different chemical compositions. Such polymers can have different solubility, mechanical property or hydrophobicity. An example is shown in Scheme II.
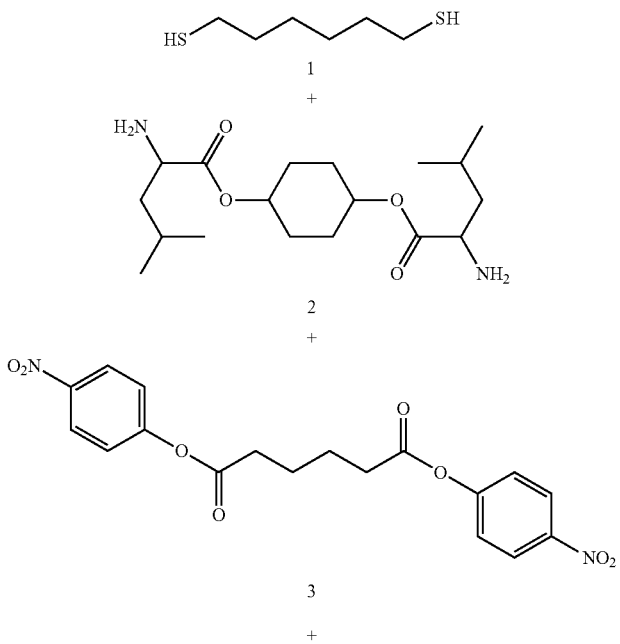

-continued

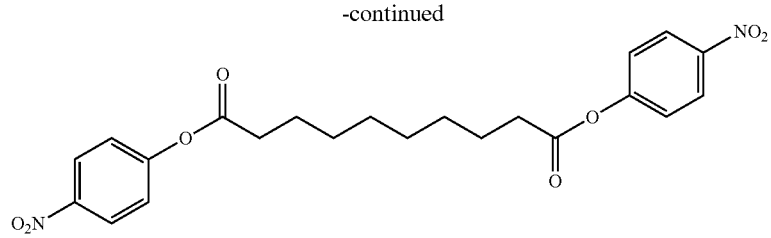

4

|NEt₃
↓DMF/65° C.

-[TE II]$_n$-[TE I]$_h$-[EA VI]$_p$-[EA VII]$_m$-

5

In some embodiments, the polymerization can occur between a dithiol, two or more diamines, and two or more activated esters. An example such polymerization is shown in Scheme III, forming -[TE II]$_n$-[TE I]$_h$-[EA VI]$_p$-[EA VII]$_m$-[EA II]$_k$-[EA I]$_o$-. The product can different $M_w$ (weight-average molecular weight) and $T_g$ depending on reaction conditions and concentration of monomers, respectively (see Example 1 and Table 9 below).

Scheme III

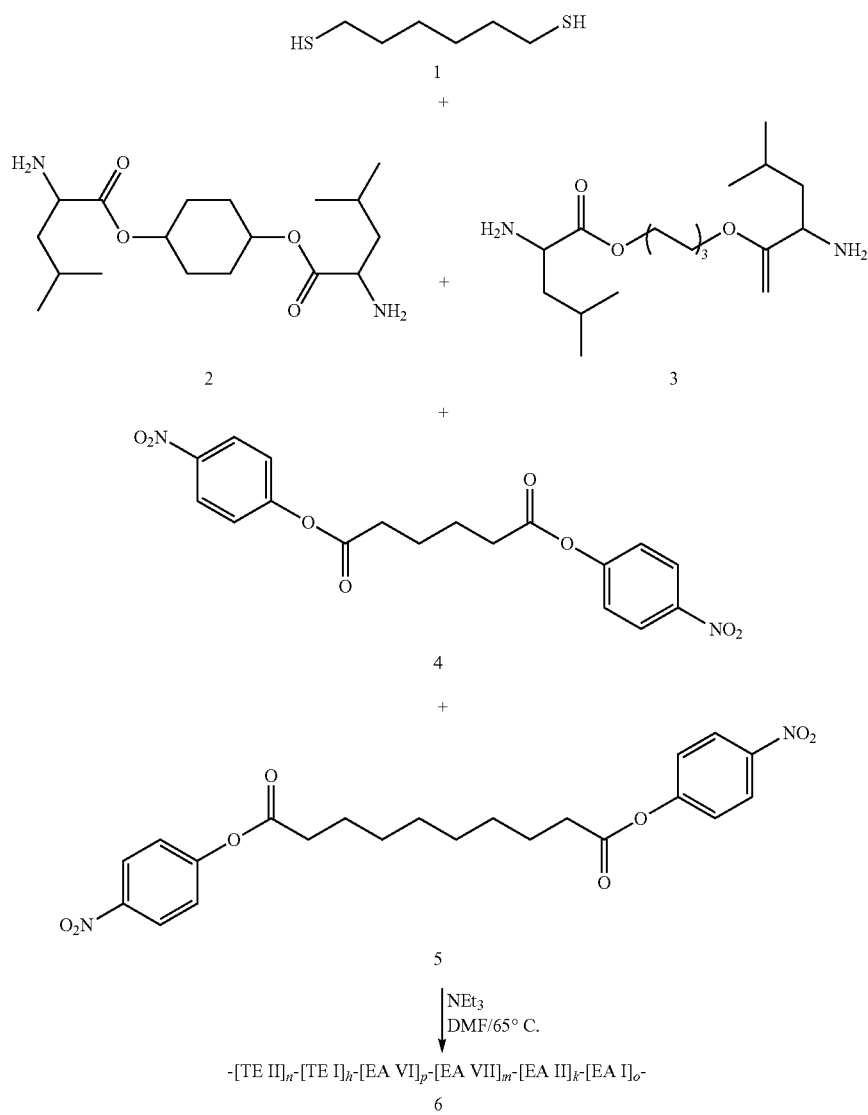

|NEt₃
↓DMF/65° C.

-[TE II]$_n$-[TE I]$_h$-[EA VI]$_p$-[EA VII]$_m$-[EA II]$_k$-[EA I]$_o$-

6

In Schemes I, II, and III, the neuclophilic agents, the dithiol and the diamine, can polymerize with the electrophilic agents dinitrophenylate with a stoichiometric ratio of the neucleophilic agents to the electrophilic agents, or vice versa. The values of n, h, p, m, k and o are as defined above. As used herein, the term stoichiometric ratio refers to a ratio of the sum of the neucleophilic agents to the sum of the electrophilic agents from about 0.99 or above to about 1.00 or below.

The neucleophilic agents can have different ratios with respect to each other. For example, the dithiol and the diamine can have a ratio from about 1:99 to about 99:1, e.g., about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, or about 95:5. Similarly, the electrophilic agents can have different ratios with respect to each other. For example, if two nitrophenylate compounds or two NHS-ester compounds are used as the electrophilic agents, the two electrophilic agents can have a ratio from about 1:99 to about 99:1, e.g., about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, or about 95:5.

In some embodiments, the PTEA polymers described herein can have an amide content at or below about 25%, for example, at or below about 10%, or at or below about 5%. The term amide content refers to the molar ratio of the amide monomer relative to other monomers in a PTEA polymer. Therefore, the amide content is the concentration of the amide monomers in a polymer relative to the total number of monomers in the polymer. In some embodiments, the amide content can be varied by varying the concentration of diamine and dithiol monomers.

In some embodiments, the electrophilic agents can be activated di-esters other than a nitrophenylate. Such activated di-esters include, but are not limited, nitrophenolate, an N-hydroxysuccinimide di-ester (NHS-di-ester) or an acyl halide.

In some embodiments, a random PTEA copolymer can be formed by reaction of an activated di-ester with an aliphatic dithiol and at least one more monomer selected from a diol, a diamine, a dicarboxylic acid, or combinations thereof. For example, a dithiol, a diol, and/or a diamine can be allowed to polymerize in dimethyl formamide (DMF) with a nitrophenolate of a diacid in the presence a base, triethyl amine, forming a random copolymer having polythioester repeating units, polyester repeating units, polyamide repeating units, poly(ester-amide) repeating units, or poly(thioester-amide) repeating units. The random copolymer can be formed using different molar ratios of dithiol, diol, or diamine monomers. For example, the dithiol can have a molar ratio ($r_n$) ranging from about 0.01 to about 0.99, the diol can have a molar ratio ($r_m$) ranging from about 0 to about 0.99, the diamine monomer can have a molar ratio ($r_k$) ranging from about 0 to about 0.99, and $r_n+r_m+r_k=1$.

The dithiol monomer generally has a formula of HS—$R_1$—SH, which is defined above.

In addition the thioester-ester-amide copolymers can be optically active by varying the ratio of the amino acid enantiomers. For example L-phenylalanine can be used rather than the racemic L,D-phenylalenine. As a result the polymers morphology will change and result in varying degradation time, drug release rate, an/or mechanical properties.

Other Polymers

A coating can be formed of the PTEA copolymer described herein alone or with one or more other polymers. Representative polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly (4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly (L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(trimethylene carbonate), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(iminocarbonate), polyurethanes, polyphosphazenes, silicones, polyesters, polyolefins, polyisobutylene and ethylene-alpha-olefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly (propylene fumarate), poly(n-butyl methacrylate), poly(sec-butyl methacrylate), poly(isobutyl methacrylate), poly(tert-butyl methacrylate), poly(n-propyl methacrylate), poly (isopropyl methacrylate), poly(ethyl methacrylate), poly (methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. PEO/PLA), polyalkylene oxides such as poly (ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the coating described herein can exclude any one of the aforementioned polymers.

In some embodiments, the coating can further include a biobeneficial material. The biobeneficial material can be polymeric or non-polymeric. The biobeneficial material is preferably substantially non-toxic, non-antigenic and non-immunogenic. A biobeneficial material is one that enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, or combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly(ethylene glycol) (PEG) or polyalkylene oxide.

Bioactive Agents

In some embodiments, a coating that includes a thioester-ester-amide copolymer described herein can optionally include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombotic, antimitotic, antibiotic, antiallergic, or antioxidant properties. Moreover, these agents can be cystostatic agents, agents that promote the healing of the endothelium, or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, dexamethasone derivatives, mometasone, meomethasone derivatives, clobetasol, other corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

In some embodiments, a coating including an thioester-ester-amide copolymers described herein can specifically exclude any one or more of the above described agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Medical Devices

As used herein, a medical device may be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, pacemaker electrodes, catheters, and endocardial leads (e.g., FINELINE and ENDOTAK, available from Guidant Corporation, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (EL-GILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable (e.g., bioabsorbable stent) or biostable polymers could also be used with the embodiments of the present invention.

Method of Use

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis.

Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, radial artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device can be implanted in any mammal, e.g., an animal or a human being. In some embodiments, the implantable device can be implanted in a patient in need of treatment by the implantable device. The treatment can be angioplasty or other type of treatments involving an implantable device.

A patient who receives the implantable device described herein can be male or female under normal body condition (e.g., normal weight) or abnormal body condition (e.g., underweight or overweight). The patient can be in any age, preferably, the patient is in an age ranging from about 40 to 70 years. An index for measuring the body condition of a patient is BMI (body mass index). A patient can have a BMI ranging from about 18 to about 30 or above.

The implantable device described herein can be used to treat or ameliorate a medical condition such as atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction, tumor obstruction, or combinations thereof

EXAMPLES

The embodiments of the present invention will be illustrated by the following prophetic examples. All parameters and data are not to be construed to unduly limit the scope of the embodiments of the invention.

Example 1

Synthesis of PEA-Hexanedithiol

A PTEA copolymer, PEA-Hexanedithiol was synthesized from a nucleophilic mixture of hexane dithiol, leucine(cyclohexanediol), and leucine(hexanediol) with stoichiometric ratio of <1.00 and >0.99 to the electrophile dinitrophenly sebacinate as the linking unit according to the reaction scheme shown in FIG. 1A.

Figure 1B:
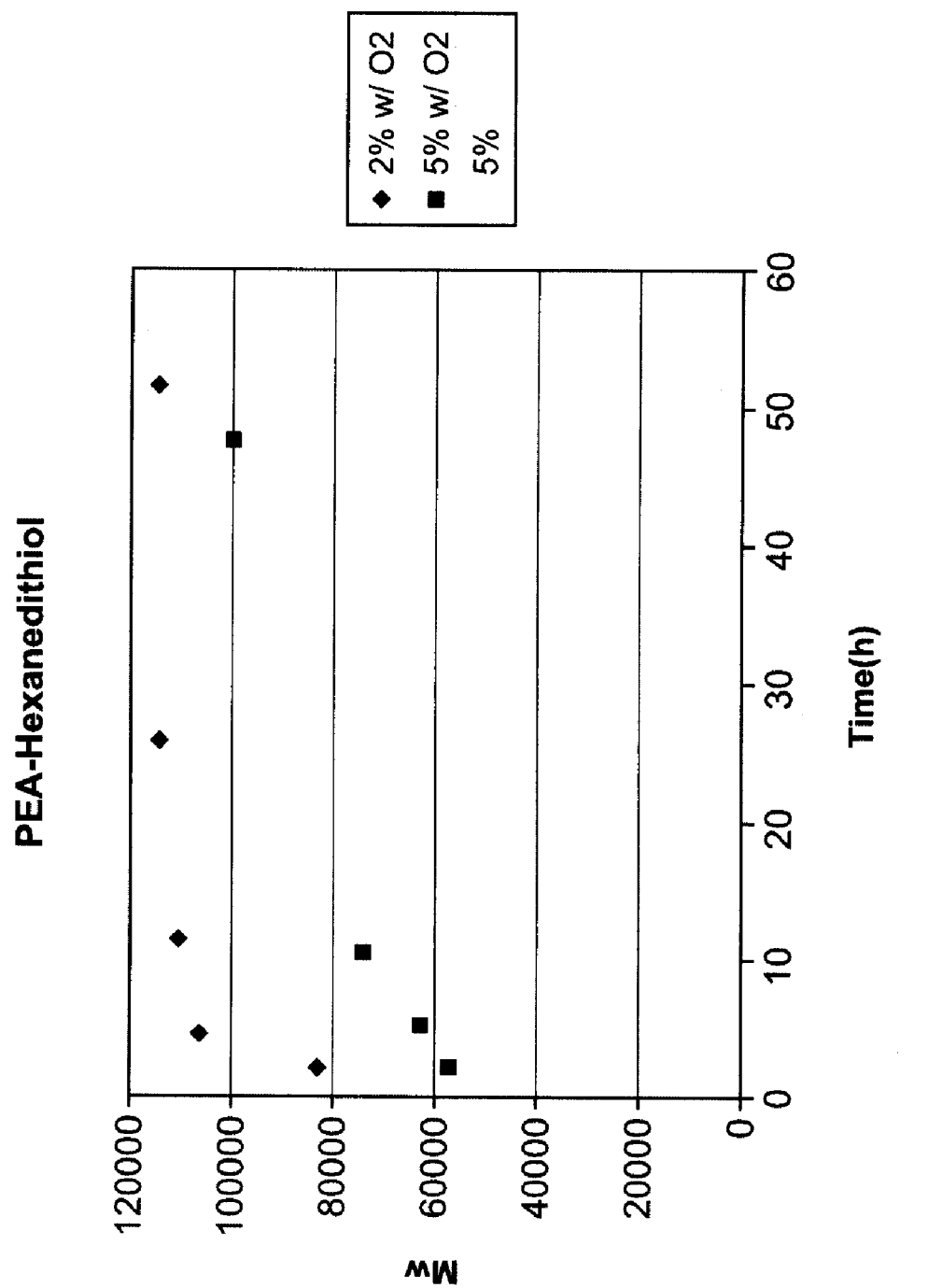
FIGS. 1B and 1C show results of molecular weight as function of reaction time for PTEA polymers.
Figure 1C:
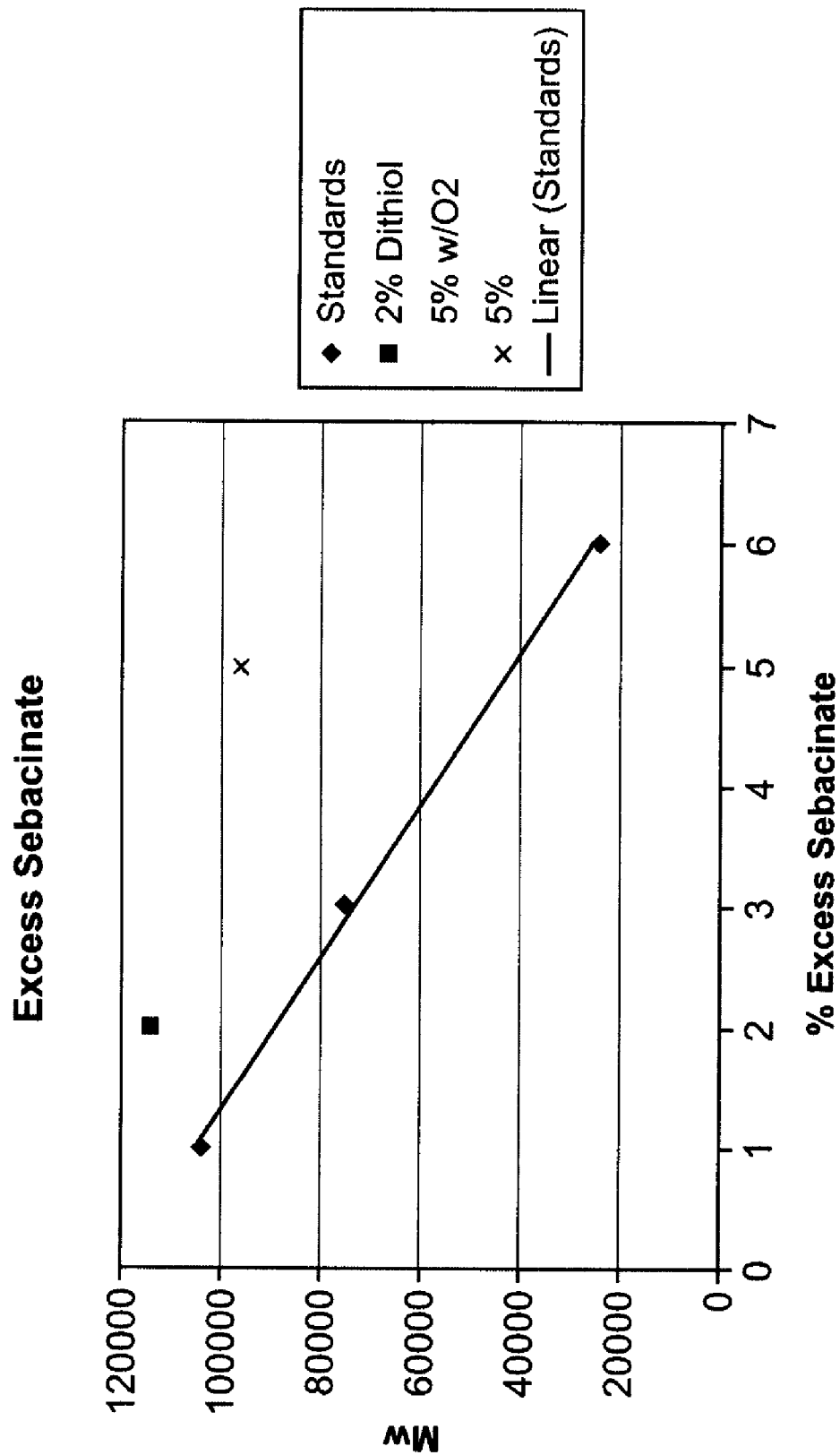

Molecular weight studies (FIGS. 1B and 1C; Table 9) show that molecular weight of polymer with the presence of the dithiol monomer is much higher, indicating that incorporation of dithiol units in the polymer was success. This is confirmed by $^1$H NMR studies (Data not shown).

TABLE 9

Molecular weight (weight average molecular weight, $M_w$) as a function of time for PEA-Hexanedithiol

| | \multicolumn{5}{c}{Time (h)} | | | | |
|---|---|---|---|---|---|
| | 2 | 4.5 | 11.5 | 26 | 52 |
| 2% with $O_2$ | 82800 | 106200 | 110200 | 114100 | 114200 |

| | \multicolumn{5}{c}{Time (h)} | | | | |
|---|---|---|---|---|---|
| | 2 | 5 | 10.5 | 24 | 48 |
| 5% with $O_2$ | 56411.5 | 61942.5 | 73260.5 | 89068 | 99650 |
| 5% | 62600 | 69600 | 78400 | 89300 | 96800 |

Example 2

Synthesis of -[TE III]$_n$-[TE I]$_h$-[EA VI]$_p$-[EA VII]$_m$-

Figure 2:
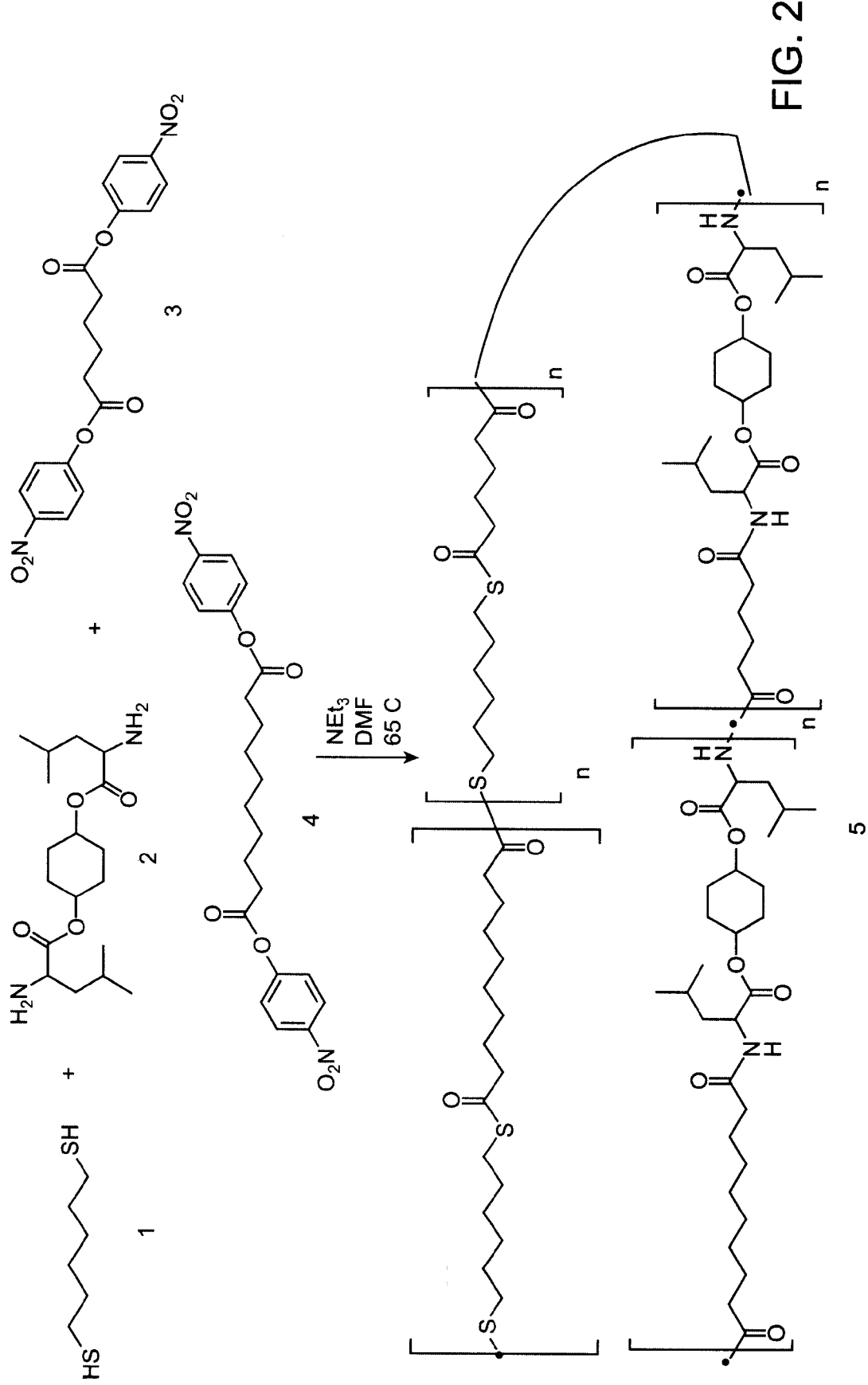
FIG. 2 shows a scheme for preparing a polymer of invention.

A PTEA copolymer, -[TE III]$_n$-[TE I]$_h$-[EA VI]$_p$-[EA VII]$_m$-, was synthesized from a nucleophilic mixture of hexane dithiol and leucine(cyclohexanediol) with stoichiometric ratio of <1.00 and >0.99 to the electrophile mixture of dinitrophenyl sebacinate and dinitrophenyl adipate as the linking units according to the reaction scheme shown in FIG. 2.

Example 3

Synthesis of -[TE III]$_n$-[TE I]$_h$-[EA VI]$_p$-[EA VII]$_n$[EA II]$_k$-[EA I]$_o$-

Figure 3:
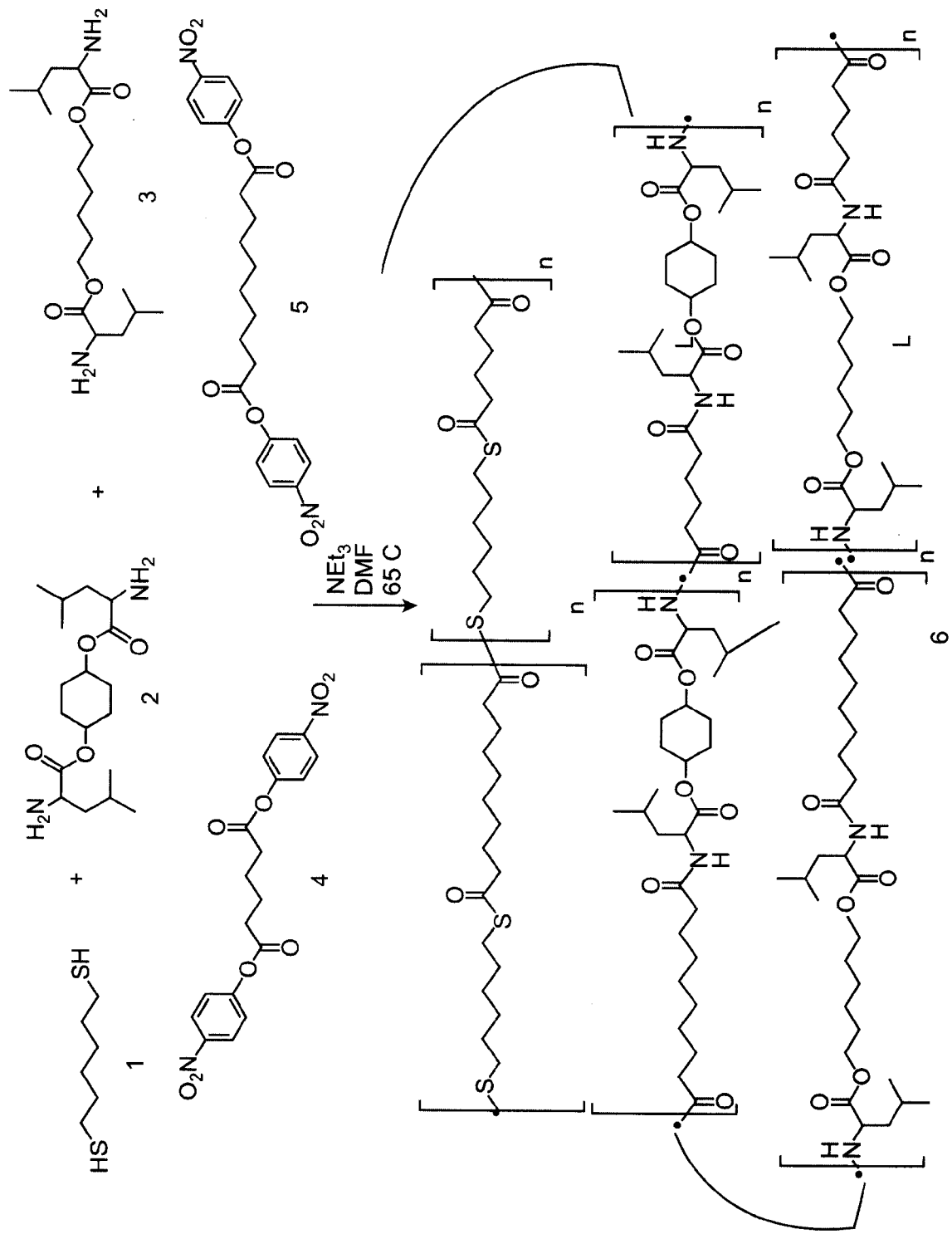
FIG. 3 shows a reaction scheme for synthesizing a PTEA polymer.

A PTEA copolymer, -[TE III]$_n$-[TE I]$_h$-[EA VI]$_p$-[EA VII]$_m$-[EA II]$_k$-[EA I]$_o$-, was synthesized from a nucleophilic mixture of hexane dithiol, leucine(cyclohexanediol), and leucine(hexanediol) with stoichiometric ratio of <1.00 and >0.99 to the electrophile mixture of dinitrophenyl sebacinate and dinitrophenyl adipate as the linking units according to the reaction scheme shown in FIG. 3.

Example 4

Synthesis of PEA-2023

PEA-2023, a PTEA copolymer, which is derived from Example 3, was synthesized from a nucleophilic mixture of exact 2.0 mmol of hexane dithiol, 5.0 mmol of leucine(cyclohexanediol), and 3.0 mmol of leucine(hexanediol) with the electrophile mixture of 5.0 mmol of dinitrophenyl sebacinate and 5.0 mmol of dinitrophenyl adipate as the linking units according to reactions similar to the scheme shown in FIG. 3. The polymer product has a weight average molecular weight ($M_w$) of 95,000 Daltons and a $T_g$ of 46° C.

Example 5

Synthesis of NDP-12

PEA-NDP-12 which is derived from Example 1, was synthesized from a nucleophilic mixture of exact 1.0 mmol of hexane dithiol, 5.0 mmol of leucine(cyclohexanediol), and 4.0 mmol of leucine(hexanediol) with the electrophile of 10.0 mmol of dinitrophenyl sebacinate as the linking units according to reactions similar to the scheme shown in FIG. 1A.

Example 6

Synthesis of NDP-17

NDP-17 which is derived from Example 1, was synthesized from a nucleophilic mixture of exact 2.5 mmol of hexane dithiol, 5.0 mmol of leucine(cyclohexanediol), and 2.5 mmol of leucine(hexanediol) with the electrophile of 10.0 mmol of dinitrophenyl sebacinate as the linking units according to reactions similar to the scheme shown in FIG. 1A.

Example 7

Mechanical Property and Drug Release Studies on a Coating Formed of -[TE I]$_n$-[EA I]$_p$-[EA VI]$_m$-

Figure 4:
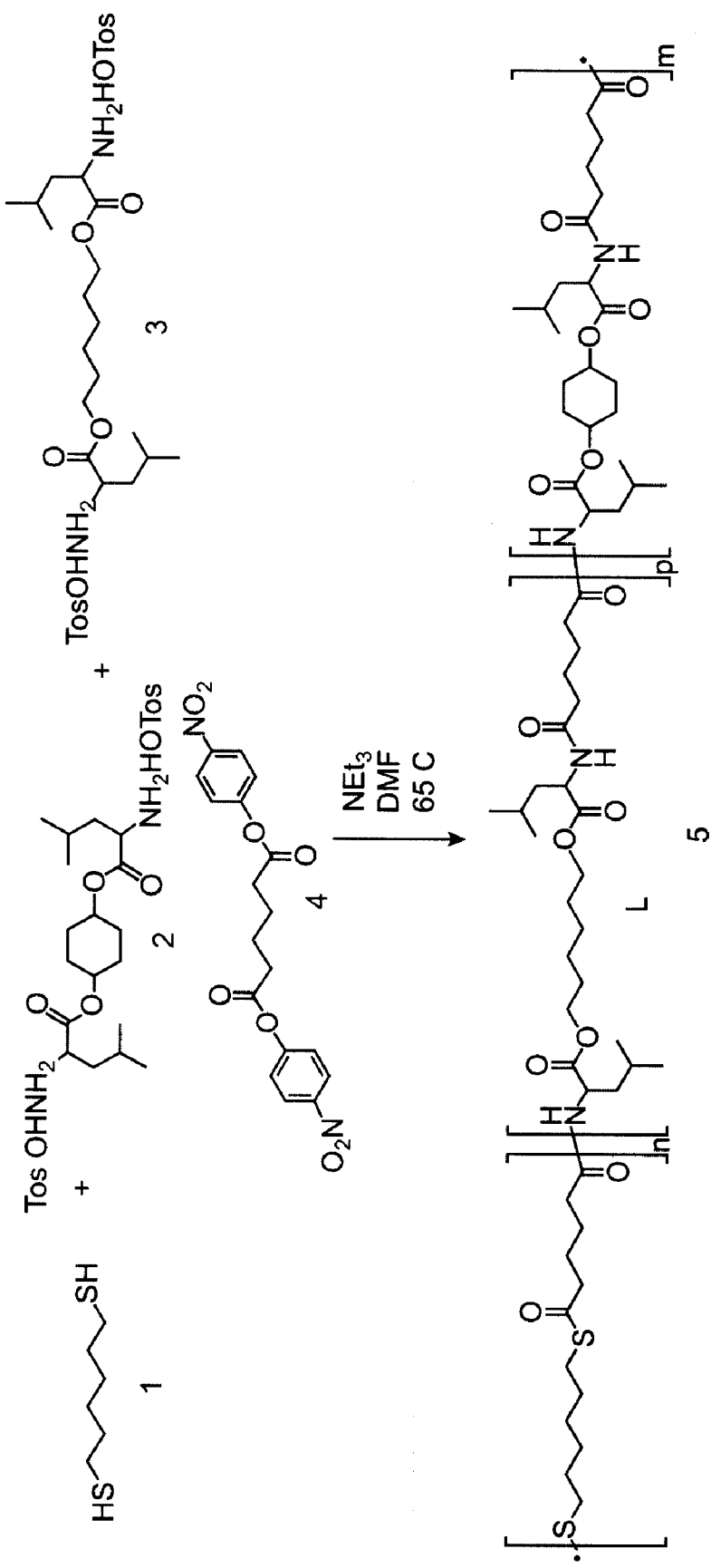
FIG. 4 shows a reaction scheme for synthesizing a PTEA polymer.

Similar to Example 4, a PTEA polymer, -[TE I]$_n$-[EA I]$_p$-[EA VI]$_m$-, was synthesized from a nucleophilic mixture of hexane dithiol, leucine(cyclohexanediol), and leucine(hexanediol) with stoichiometric ratio of <1.00 and >0.99 to the electrophile dinitrophenly adipate as the linking unit according to the reaction scheme shown in FIG. 4.

Example 8

Water Uptake Studies on PTEA Copolymers

Figure 5:
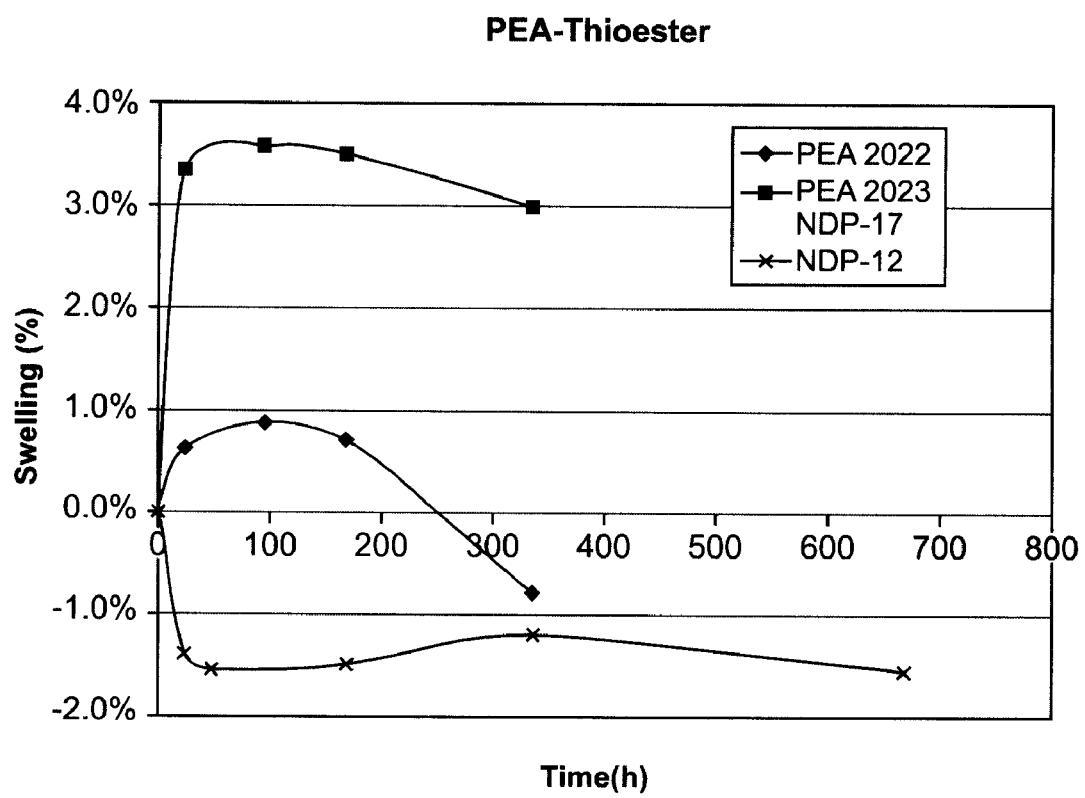
FIG. 5 shows the result of water uptake study on PTEA polymers.

The PTEA polymer synthesized according to FIG. 3 (PEA2022), which comprising adipate and sebacinate units (linkages) and PEA2023, which is synthesized according to a reaction scheme similar to the one shown in FIG. 3 (with sebacinate only linkages instead of adipate and sebacinate linkages), and NDP-12 and NDP 17, made above, were subject to water uptake studies. The results are shown in FIG. 5, which shows that PEA2022 swells significantly more than other polymers due to its randomized structure comprising both adipate and sebacinate linkages.

Discussion

By using a mixture of electrophiles to synthesize PTEA polymers, there is an inherent disorder in the PTEA polymer chains. The data in FIG. 5 shows that this disorder increases the polymer's water uptake in that a polymer reduces the ability to organize itself even in the amorphous state and as a result increases its free volume. When the polymer is immersed in water, water is then better able to penetrate the polymer, leading to increased swelling of the polymer, which in turn will lead to an increase in the degradation rate of the polymer.

Example 9

Water Uptake Studies on PTEA Copolymers

PTEA polymers having a general formula of -[TE I]$_n$-[EA I]$_p$-[EA VI]$_m$-, which were prepared according to Example 7 using different ratios of p to m (p/m), were used to form coatings on stents. Mechanical studies and drug (everolimus) release rate (RR) studies on the coatings were performed. The scanning electronic micrograph (SEM) images were shown in FIG. 6. Results of such studies are summarized in Table 10.

TABLE 10

| PTEA polymer | p/m ratio | $T_g$ (° C.) | drug release rate (RR) in 3 day (in % of drug load) |
|---|---|---|---|
| 8167-40 | 1:1 | 49 | 19.9 |
| 8167-41 | PEG* | 57 | 19.9 |
| 8167-42 | 1:3 | 59 | 7.1 |
| 8167-33 | 0:1 | 83 | 7.2 |

*EA I and EA VI units are replaced with poly(ethylene glycol) (PEG).

Figure 6:
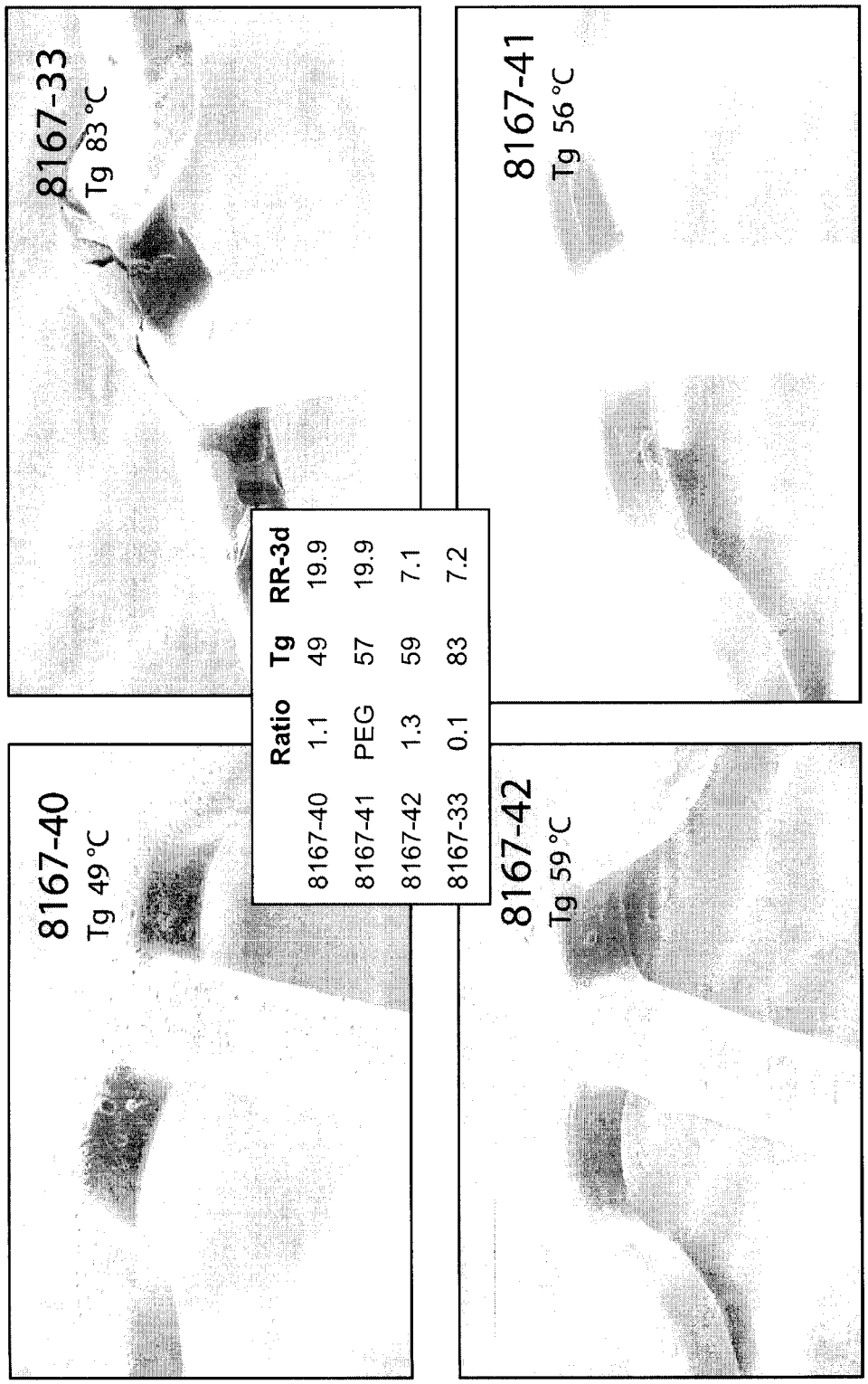
FIG. 6 shows scanning electronic micrograph (SEM) images of several PTEA polymers.

FIG. 6 shows that a coating formed of 8167-33 has an unsatisfactory coating integrity and that a coating formed of 8167-42 has a good coating integrity. The release rate of everolimus can be controlled by varying p/m ratio in the PTEA polymer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A poly(thioester amide) copolymer wherein the copolymer comprises thioester units and amide units in the backbone of the copolymer; and wherein the thioester units comprise a structure of Formula I:

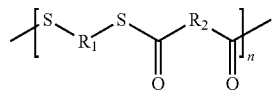

Formula I wherein $R_1$ is an aliphatic group,
wherein $R_2$ is a straight chained aliphatic group, a branch chained aliphatic group, a cyclic aliphatic group, an aliphatic group including heteroatom(s) selected from oxygen, F, Cl, Br, I,S ,N ,phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and
wherein n is a positive integer from 1 to about 10,000.

2. A poly(thioester amide) copolymer wherein the copolymer comprises thioester units and amide units in the backbone of the copolymer; and wherein the thioester units comprise a structure selected from

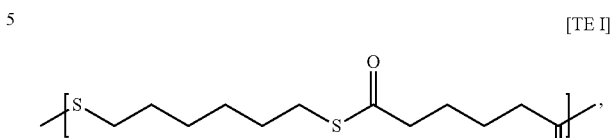
[TE I]

[TE II]

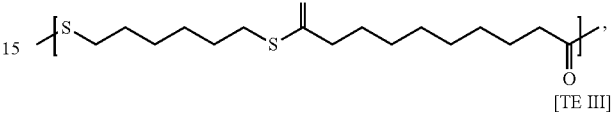
[TE III]

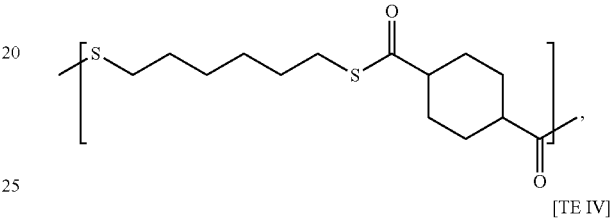
[TE IV]

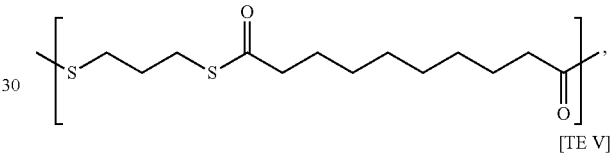
[TE V]

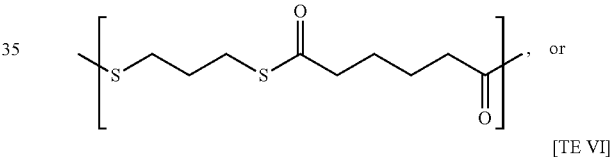
, or [TE VI]

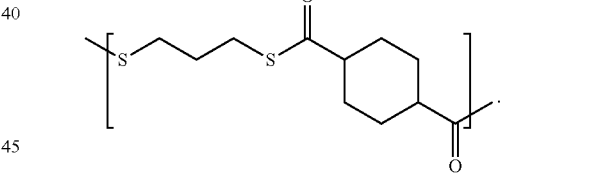

3. The copolymer of claim 1, wherein the copolymer is a random, alternating, or block copolymer.

4. The copolymer of claim 1, comprising at least one ester amide units comprising a structure selected from

[EA I]

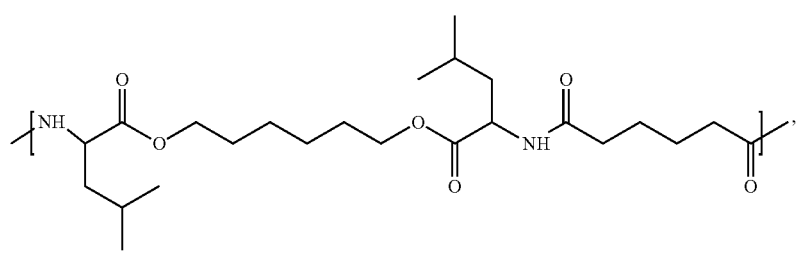

-continued

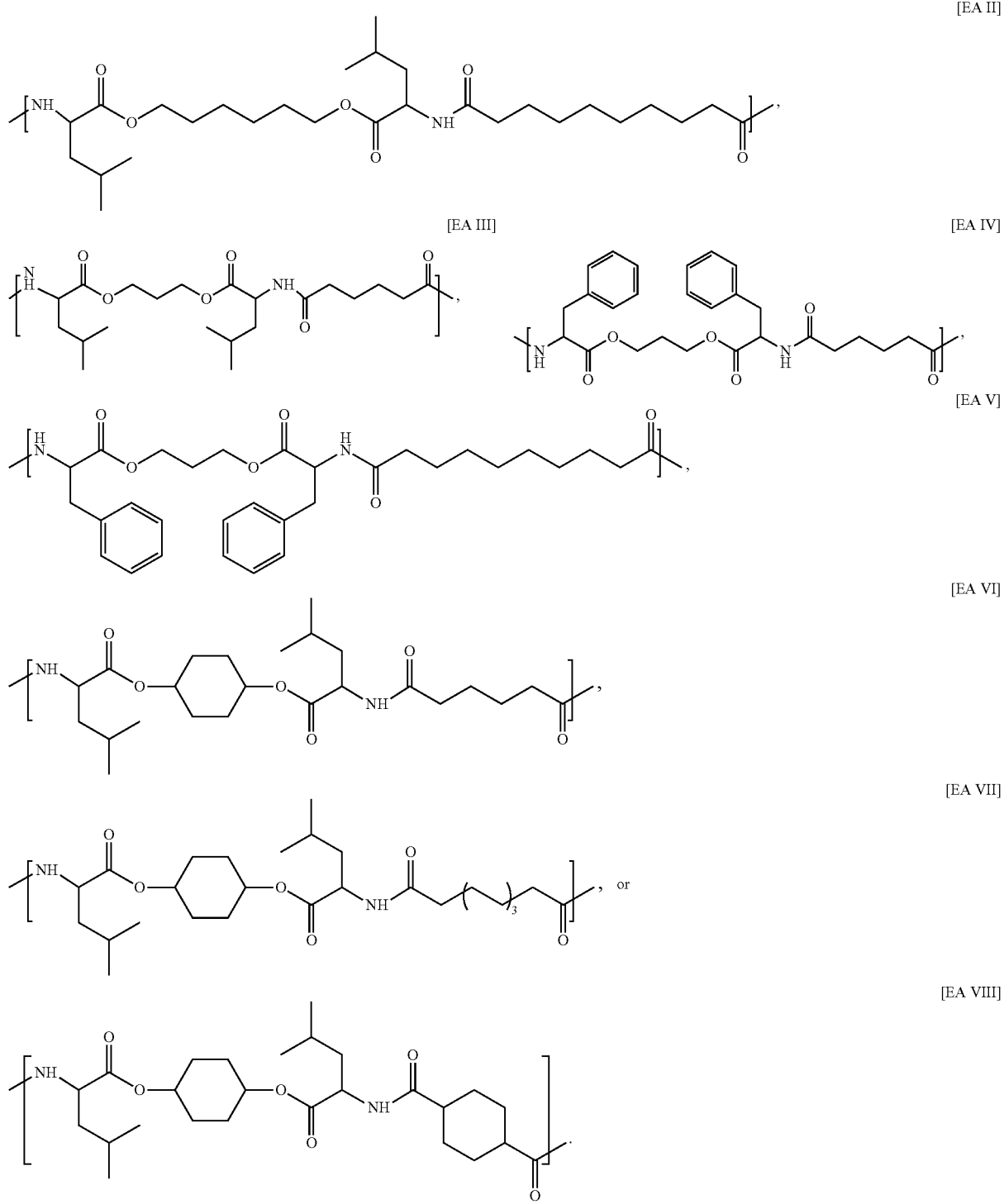

5. The copolymer of claim 1, having a formula selected from
-[TE I]$_n$-[EA I]$_p$-[EA IV]$_m$-,
-[TE I]$_n$-[EA III]$_p$-[EA IV]$_m$-,
-[TE I]$_n$-[EA I]$_p$-[EA VI]$_m$-,
-[TE I]$_n$-[EA I]$_p$-,
-[TE I]$_n$-[EA III]$_p$-,
-[TE I]$_n$-[EA IV]$_p$-,
-[TE I]$_n$-[EA VI]$_p$-,
-[TE II]$_n$-[EA II]$_p$[EA IV]$_m$-,
-[TE II]$_n$-[EA II]$_p$-[EA VII]$_m$-,
-[TE II]$_n$-[EA II]$_p$-,
-[TE II]$_n$-[EA VII]$_p$-,
-[TE II]$_n$-[EA V]$_p$-,
-[TE II]$_n$-[EA V]$_p$-,
-[TE II]$_n$-[TE I]$_n$-[EA IV]$_p$-[EA V]$_m$-, or
-[TE II]$_n$-[TE I]$_n$-[EA VI]$_p$-[EA VIII]$_m$-[EA II]$_k$-[EA I]$_o$-,
-[TE I]$_n$-[TE V]$_o$-[EA I]$_p$-[EA IV]$_m$-, -[TE I]$_n$-[TE V]$_o$-[EA II]$_p$-[EA IV]$_m$-,
-[TE I]$_n$-[TE V]$_o$-[EA II]$_p$-[EA VI]$_m$-,
-[TE I]$_n$-[TE V]$_o$-[EA I]$_p$-,
-[TE I]$_n$-[TE V]$_o$-[EA III]$_p$-,
-[TE I]$_n$-[TE V]$_o$-[EA IV]$_p$-,
-[TE I]$_n$-[TE V]$_o$-[EA VI]$_p$-,
-[TE II]$_n$-[TE IV]$_o$-[EA II]$_p$[EA IV]$_m$-,
-[TE II]$_n$-[TE IV]$_o$-[EA II]$_p$-[EA VII]$_m$-,
-[TE II]$_n$-[TE IV]$_o$-[EA II]$_p$-,
-[TE II]$_n$-[TE IV]$_o$-[EA VII]$_p$-,
-[TE II]$_n$-[TE IV]$_o$-[EA V]$_p$-,
-[TE II]$_n$-[TE IV]$_o$-[EA V]$_p$-,
-[TE II]$_n$-[TE I]$_h$-[TE IV]$_g$-[TE V]$_o$-[EA IV]$_p$-[EA V]$_m$-, or
-[TE II]$_n$-[TE I]$_h$-[TE IV]$_g$-[TE V]$_o$-[EA VI]$_p$-[EA VII]$_m$-[EA II]$_k$-[EA I]$_f$, wherein n, g, j, and h are independent integers from 0 to about 10,000;

p, m and o are independent integers from 0 to about 10,000;

the sum of $n+h+g+o \geq 1$; and the sum of $p+m+f+k \geq 1$.

6. The copolymer of claim 1, wherein at least one activated di-acid is in a stoichiometric molar ratio to the sum of at least one dithiol, the diol(s) and/or the diamine(s).

7. The copolymer of claim 6, wherein, among the at least one dithiol, the diol(s) and/or diamine(s): the at least one dithiol has a molar ratio ($r_n$) from about 0.01 to 0.99 the diol(s) has a molar ratio ($r_m$) from about 0 to about 0.99, the diamine(s) has a molar ratio ($r_k$) from about 0 to about 0.99, and $r_n+r_m+r_K=1$.

8. The copolymer of claim 1, comprising an amide content of about 25% or less.

9. The copolymer of claim 1, comprising an amide content of about 10% or less.

10. A coating on an implantable medical device, comprising a poly(thioester amide) copolymer wherein the copolymer comprises thioester units and amide units in the backbone of the copolymer; and wherein the thioester units comprise a structure of Formula I:

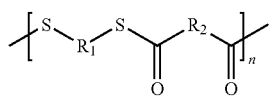

Formula I wherein $R_1$ is an aliphatic group, wherein $R_2$ is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and wherein n is a positive integer from 1 to about 10,000.

11. A coating on a medical device comprising a poly(thioester amide) copolymer wherein the copolymer comprises thioester units and amide units in the backbone of the copolymer; and wherein the thioester units comprise a structure selected from

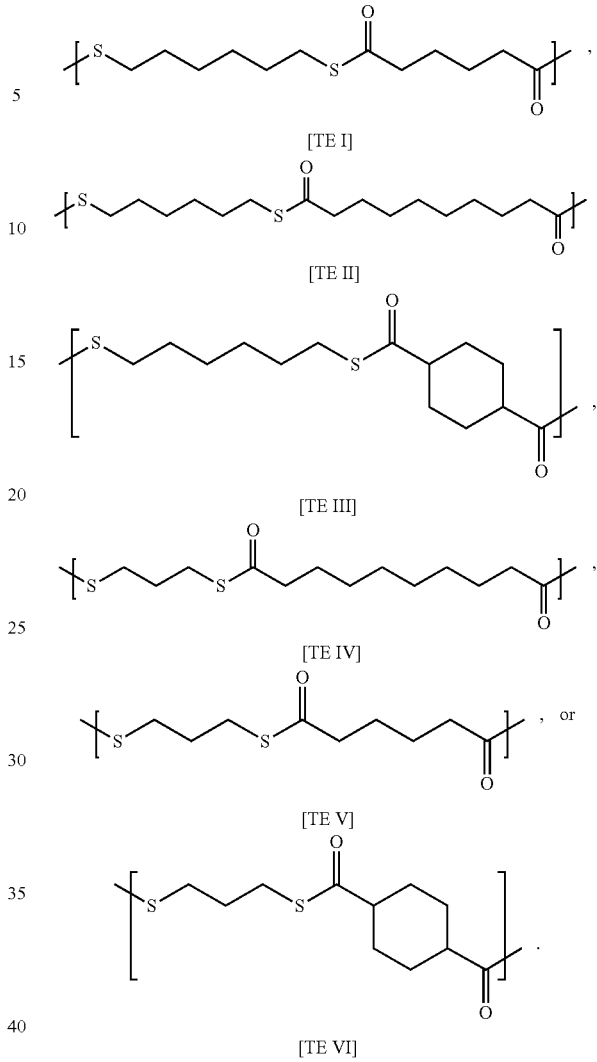

12. A coating on an implantable device, comprising a poly(thioester amide) copolymer wherein the copolymer comprises thioester units and amide units in the backbone of the copolymer; wherein the thioester units comprise a structure of Formula I:

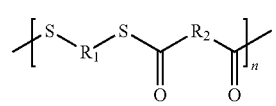

Formula I wherein $R_1$ is an aliphatic group, wherein $R_2$ is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and wherein n is a positive integer from 1 to about 10,000;

and wherein the copolymer comprises one ester amide units comprising a structure selected from

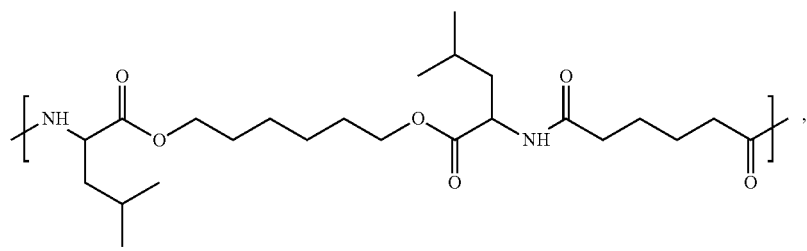
[EA I]
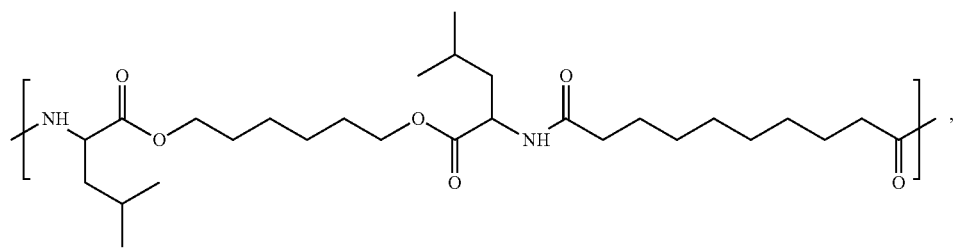
[EA II]
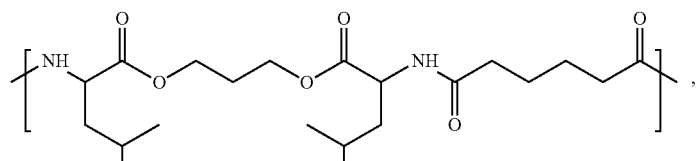
[EA III]
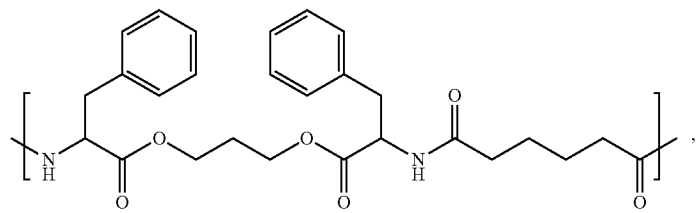
[EA IV]
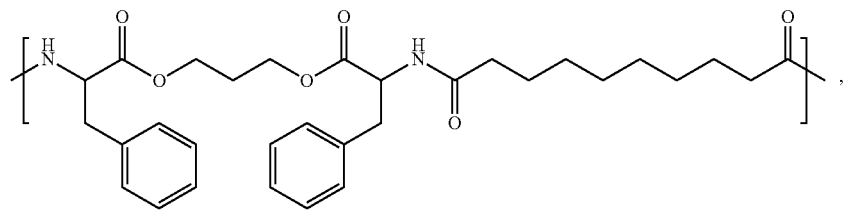
[EA V]
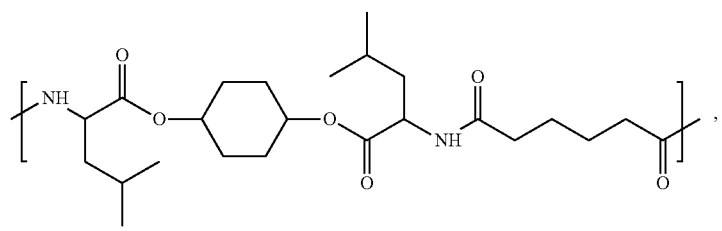
[EA VI]

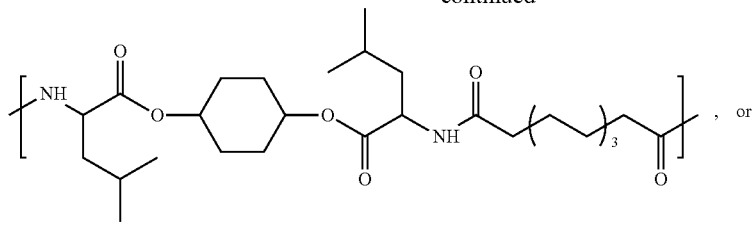

[EA VII]

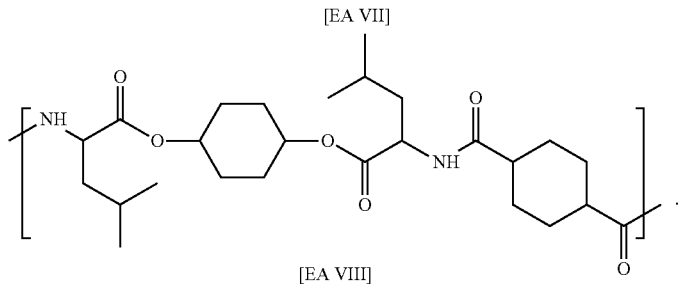

[EA VIII]

13. A coating on an implantable device, comprising a poly(thioester amide) copolymer wherein the copolymer comprises thioester units and amide units in the backbone of the copolymer; and wherein the thioester units comprise a structure of Formula I:

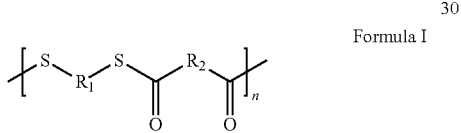

Formula I wherein $R_1$ is an aliphatic group,
wherein $R_2$ is an O, F, Cl, Br, I, S, N, phenyl or naphthyl;
wherein n is a positive integer from 1 to about 10,000;
and wherein the copolymer has a formula selected from
-[TE I]$_n$-[EA I]$_p$-[EA IV]$_m$-,
-[TE I]$_n$-[EA III]$_p$-[EA IV]$_m$-,
-[TE I]$_n$-[EA II]$_p$-[EA VI]$_m$-,
-[TE I]$_n$-[EA II]$_p$-,
-[TE I]$_n$-[EA III]$_p$-,
-[TE I]$_n$-[EA IV]$_p$-,
-[TE I]$_n$-[EA VI]$_p$-,
-[TE II]$_n$-[EA II]$_p$[EA IV]$_m$-,
-[TE II]$_n$-[EA II]$_p$-[EA VII]$_m$-,
-[TE II]$_n$-[EA II]$_p$-,
-[TE II]$_n$-[EA VII]$_p$-,
-[TE II]$_n$-[EA V]$_p$-,
-[TE II]$_n$-[EA V]$_p$-,
-[TE II]$_n$-[TE I]$_h$-[EA IV]$_p$-[EA V]$_m$-, or
-[TE III]$_n$-[TE I]$_h$-[EA VI]$_p$-[EA VII]$_m$-[EA II]$_k$-[EA I]$_o$-,
-[TE I]$_n$-[TE V]$_o$-[EA II]$_p$-[EA IV]$_m$-,
-[TE I]$_n$-[TE V]$_o$-[EA III]$_p$-[EA IV]$_m$-,
-[TE I]$_n$-[TE V]$_o$-[EA II]$_p$-[EA VI]$_m$-,
-[TE I]$_n$-[TE V]$_o$-[EA II]$_p$-,
-[TE I]$_n$-[TE V]$_o$-[EA III]$_p$-,
-[TE I]$_n$-[TE V]$_o$-[EA IV]$_p$-,
-[TE I]$_n$-[TE V]$_o$-[EA VI]$_p$-,
-[TE II]$_n$-[TE IV]$_o$-[EA II]$_p$[EA IV]$_m$-,
-[TE II]$_n$-[TE IV]$_o$-[EA II]$_p$-[EA VII]$_m$-,
-[TE II]$_n$-[TE IV]$_o$-[EA II]$_p$-,
-[TE II]$_n$-[TE IV]$_o$-[EA VII]$_p$-,
-[TE II]$_n$-[TE IV]$_o$-[EA V]$_p$-,
-[TE II]$_n$-[TE IV]$_o$-[EA V]$_p$-,
-[TE III]$_n$-[TE I]$_h$-[TE IV]$_g$-[TE V]$_o$-[EA IV]$_p$-[EA V]$_m$-, or
-[TE II]$_n$-[TE I]$_h$-[TE IV]$_g$-[TE V]$_o$-[EA VI]$_p$-[EA VII]$_m$-[EA II]$_k$-[EA I]$_f$-, wherein:
n, g, j, and h are independent integers from 0 to about 10,000;
p, m and o are independent integers from 0 to about 10,000;
the sum of n+h+g+o≧1; and
the sum of p+m+f+k≧1.

14. A coating on an implantable device, comprising a poly(thioester amide) copolymer wherein the copolymer comprises thioester units and amide units in the backbone of the copolymer; wherein the thioester units comprise a structure of Formula I:

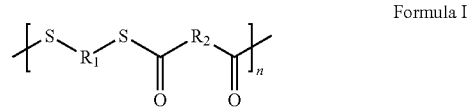

Formula I wherein $R_1$ is an aliphatic group,
wherein $R_2$ is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and
wherein n is a positive integer from 1 to about 10,000;
and wherein at least one activated di-acid is in a stoichiometric molar ratio to the sum of at least one dithiol, the diol(s) and/or the diamine(s).

15. The coating of claim 14, wherein, among the at least one dithiol, the diol(s) and/or diamine(s): the at least one dithiol has a molar ratio ($r_n$) from about 0.01 to 0.99. the diol(s) has a molar ratio ($r_m$) from about 0 to about 0.99, the diamine(s) has a molar ratio ($r_k$) from about 0 to about 0.99, and $r_n+r_m+r_K=1$.

16. A coating on an implantable device, comprising a poly(thioester amide) copolymer wherein the copolymer comprises thioester units and amide units in the backbone of the copolymer; wherein the thioester units comprise a structure of Formula I:

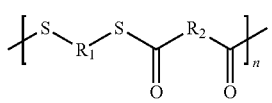

Formula I wherein $R_1$ is an aliphatic group,
wherein $R_2$ is a straight chained aliphatic group, a branch chained aliphatic group, a cyclic aliphatic group, an aliphatic group including heteroatom(s) selected from oxygen, F, Cl, Br, I ,S ,N, phenyl ,naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and
wherein n is a positive integer from 1 to about 10,000;
and wherein the copolymer comprises an amide content of about 25% or less.

17. A coating on an implantable device, comprising a poly(thioester amide) copolymer wherein the copolymer comprises thioester units and amide units in the backbone of the copolymer; wherein the thioester units comprise a structure of Formula I:

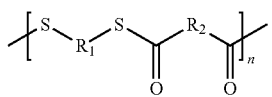

Formula I wherein $R_1$ is an aliphatic group,
wherein $R_2$ is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and
wherein n is a positive integer from 1 to about 10,000;
and wherein the copolymer comprises an amide content of about 10% or less.

18. A coating on an implantable device, comprising a poly(thioester amide) copolymer and a bioactive agent, wherein the copolymer comprises thioester units and amide units in the backbone of the copolymer; wherein the thioester units comprise a structure of Formula I:

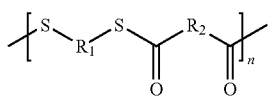

Formula I wherein $R_1$ is an aliphatic group,
wherein $R_2$ is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and
wherein n is a positive integer from 1 to about 10,000.

19. The coating of claim 18, wherein the bioactive agent is selected from paclitaxel, docetaxel, estradiol, nitric oxide donors, super oxide dismutases, super oxide dismutases mimics, 4-amino-2,2,6,6-tetramethylpoperidine-1-oxyl (4-amino-TEMPO), tacrolimus, dexamethasone, dexamethasone acetate, other dexamethasone derivatives, rapamycin, rapamycin derivatives, 40-O-(2-hydroxy)ethyl-rapamycin, 40-O-(3-hydroxy)propyl-rapamycin, 40-O-[2-(2-hydroxy)ethyoxy]ethyl-rapamycin, 40-O-tetrazole-rapamycin, 40-epi-(N1-tetrazolyl)-rapamycin, TAFA-93, biolimus-7, biolimus-9, clobetasol, momethasone derivatives, pimecrolimus, imatinib mesylate, midostaurin, or combinations thereof.

20. The coating of claim 19, wherein the bioactive agent is everolimus.

21. A coating on an implantable device, comprising a poly(thioester amide) copolymer wherein the copolymer comprises thioester units and amide units in the backbone of the copolymer; wherein the thioester units comprise a structure of Formula I:

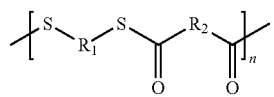

Formula I wherein $R_1$ is an aliphatic group,
wherein $R_2$ is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and
wherein n is a positive integer from 1 to about 10,000,
wherein the medical device is a stent.

22. The coating of claim 21, wherein the medical device is a bioabsorbable stent.

23. A medical device comprising a poly(thioester amide) copolymer wherein the copolymer comprises thioester units and amide units in the backbone of the copolymer; wherein the thioester units comprise a structure of Formula I:

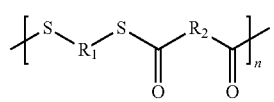

Formula I wherein $R_1$ is an aliphatic group,
wherein $R_2$ is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, wherein n is a positive integer from 1 to about 10,000.

24. The medical device of claim 23, further comprising a bioactive agent.

25. The medical device of claim 23, which is a bioabsorbable stent.

26. The medical device of claim 23, which is a drug delivery matrix.

27. The medical device of claim 26, which is a hydrogel.

28. A composition comprising a poly(thioester amide) copolymer wherein the copolymer comprises thioester units and amide units in the backbone of the copolymer; wherein the thioester units comprise a structure of Formula I:

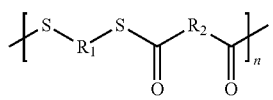

Formula I wherein $R_1$ is an aliphatic group, wherein $R_2$ is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, wherein n is a positive integer from 1 to about 10,000.

29. The composition of claim 28, further comprising a bioactive agent.

30. The composition of claim 29, which is a bioabsorbable stent.

31. The composition of claim 29, which is a drug delivery matrix.

32. The composition of claim 31, which is a hydrogel.

33. A method of treating a medical condition comprising implanting in a human being a medical device comprising a coating that comprises a poly(thioester amide) copolymer wherein the copolymer comprises thioester units and amide units in the backbone of the copolymer; wherein the thioester units comprise a structure of Formula I:

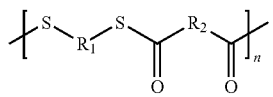

Formula I wherein $R_1$ is an aliphatic group, wherein $R_2$ is a straight chained aliphatic group, a branch chained aliphatic group, a cyclic aliphatic group, an aliphatic group including heteroatom(s) selected from oxygen, F, Cl, Br, I, S,N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, wherein n is a positive integer from 1 to about 10,000, and wherein the medical condition is selected from atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

34. A method of treating a medical condition, comprising implanting in a human being a medical device comprising a coating that comprises a poly(thioester amide) copolymer and a bioactive agent, wherein the copolymer comprises thioester units and amide units in the backbone of the copolymer; wherein the thioester units comprise a structure of Formula I:

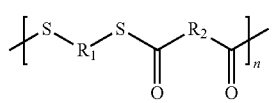

Formula I wherein $R_1$ is an aliphatic group, wherein is a straight chained aliphatic group, a branch chained aliphatic group, a cyclic aliphatic group, an aliphatic group including heteroatom(s) selected from oxygen, F, Cl, Br, I, S, N, phenyl, naphthyl, or an aliphatic group having substituent(s) selected from alkyl, F, Cl, Br, I, carboxyl, hydroxyl, phosphoryl, sulfonyl, carbonyl, amino, amide, ether, nitro, azo, or combinations thereof, and wherein n is a positive integer from 1 to about 10,000, and wherein the medical condition is selected from atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

* * * * *